(12) United States Patent
Yanaki

(10) Patent No.: US 9,956,403 B2
(45) Date of Patent: May 1, 2018

(54) ACTIVE TRANSDERMAL MEDICAMENT PATCH AND CIRCUIT BOARD FOR SAME

(71) Applicant: Activatek, Inc., Salt Lake City, UT (US)

(72) Inventor: Jamal S. Yanaki, Salt Lake City, UT (US)

(73) Assignee: Activatek, Inc., Gilroy, CA (US)

( * ) Notice: Subject to any disclaimer, the term of this patent is extended or adjusted under 35 U.S.C. 154(b) by 694 days.

(21) Appl. No.: 14/507,483

(22) Filed: Oct. 6, 2014

(65) Prior Publication Data

US 2015/0025441 A1   Jan. 22, 2015

Related U.S. Application Data

(63) Continuation of application No. 12/009,443, filed on Jan. 18, 2008, now Pat. No. 8,862,223.

(51) Int. Cl.

| A61N 1/30 | (2006.01) |
|---|---|
| A61K 9/70 | (2006.01) |
| A61N 1/04 | (2006.01) |
| A61N 1/32 | (2006.01) |
| A61N 1/08 | (2006.01) |

(52) U.S. Cl.
CPC ............ *A61N 1/303* (2013.01); *A61K 9/7023* (2013.01); *A61N 1/044* (2013.01); *A61N 1/0448* (2013.01); *A61N 1/08* (2013.01); *A61N 1/325* (2013.01)

(58) Field of Classification Search
CPC ...... A61N 1/303; A61N 1/044; A61N 1/0448; A61N 1/08; A61N 1/325; A61K 9/7023

USPC .................................................... 604/19–20
See application file for complete search history.

(56) References Cited

U.S. PATENT DOCUMENTS

| 4,865,582 | A | * | 9/1989 | Sibalis | ................... | A61N 1/044 604/20 |
|---|---|---|---|---|---|---|
| 4,942,883 | A | * | 7/1990 | Newman | ................ | A61N 1/044 424/449 |
| 5,688,232 | A | * | 11/1997 | Flower | ..................... | A61N 1/30 604/20 |
| 6,169,920 | B1 | * | 1/2001 | Haak | .................... | A61N 1/0436 604/20 |

(Continued)

*Primary Examiner* — Manuel Mendez
(74) *Attorney, Agent, or Firm* — Hanson Bridgett LLP; Russell C. Petersen

(57) ABSTRACT

An active transdermal medicament patch includes a planar substrate with a therapeutic face releasably retainable against the skin of a patient. A return electrode and a medicament matrix susceptible to permeation by medicament are secured at separated locations on the therapeutic face and electrically conductively engage the skin. A detector monitors iontophoretic medicament migration into the skin. An integrator operating on the output of the detector produces a running cumulative total of the amount of medicament delivered during a plurality of temporally non-contiguous therapy subsessions. A circuit breaker terminates medicament migration, when the output of the integrator equals a predetermined medicament quantity. A timer active during medicament migration stimulates a driver to operate a light-emitting diode in a distinct delivery confirmation mode during each a sequence of non-overlapping predetermined therapy subsessions, respectively. A circuit board on the substrate in a compact, folded state bears interconnected electrical circuit components.

30 Claims, 10 Drawing Sheets

(56) References Cited

U.S. PATENT DOCUMENTS 8,862,223 B2 * 10/2014 Yanaki ................. A61K 9/7023
424/449

* cited by examiner

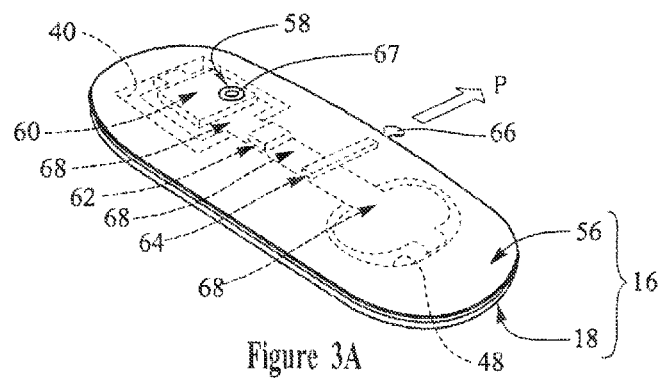
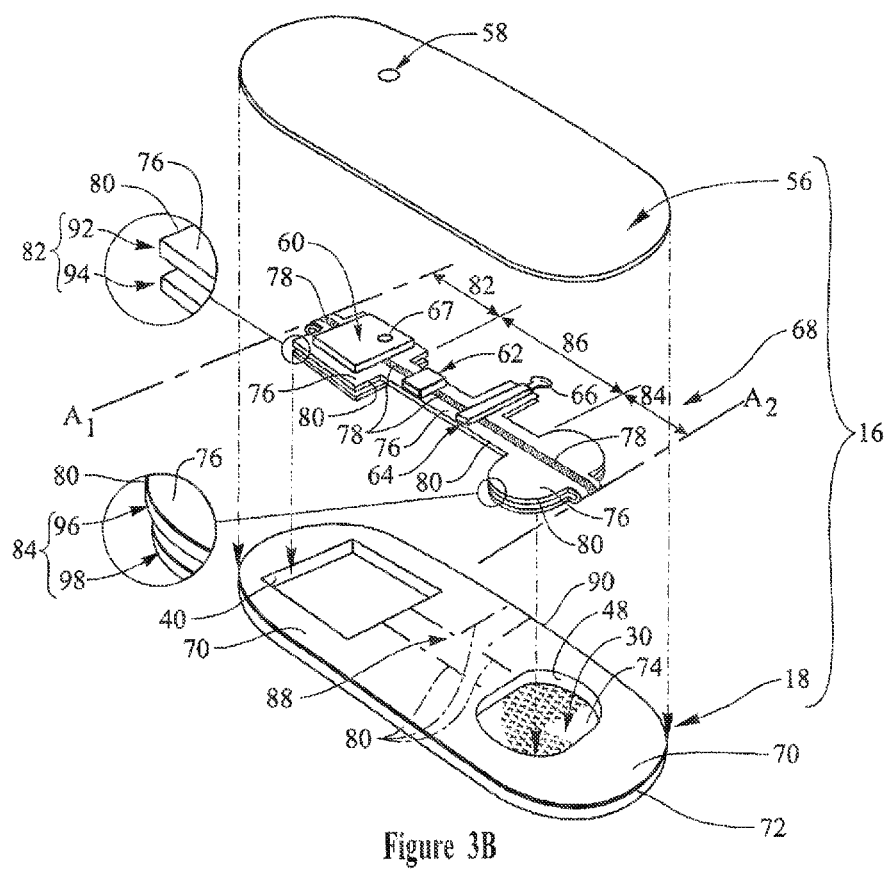
Figure 3A
Figure 3B

ACTIVE TRANSDERMAL MEDICAMENT PATCH AND CIRCUIT BOARD FOR SAME

RELATED APPLICATIONS

This application is a continuation of U.S. patent application Ser. No. 12/009,443 that was filed on Jan. 18, 2008 and issued on Oct. 14, 2014 as U.S. Pat. No. 8,862,223, which is related to: (1) U.S. Design patent application Ser. No. 29/261,600 that was filed on Jun. 16, 2006, and that issued on Sep. 2, 2008 as U.S. Design Pat. No. D576,282 for a design titled "Adhesive Transdermal Medicament Patch"; (2) U.S. patent application Ser. No. 11/701,749 that was filed on Feb. 2, 2007, for an invention titled "Active Iontophoresis Delivery System." (3) U.S. patent application Ser. No. 11/811,241 that was filed on Jun. 8, 2007, and that issued on Jun. 12, 2012 as U.S. Pat. No. 8,197,844 for an invention titled "Active Electrode For Transdermal Medicament Administration"; and (4) U.S. patent application Ser. No. 11/701,749 that was filed on Feb. 2, 2007 for an invention titled "Active Iontophoresis Delivery System."

BACKGROUND

Field of the Invention

The invention disclosed herein relates to the transdermal administration of medicaments to human and animal subjects. More particularly, the present invention pertains to active iontophoretic delivery systems in which electrical contacts are applied to the surface of the skin of a subject for the purpose of delivering medicament through the surface of the skin into underlying tissue.

Background Art

During active iontophoresis, direct electrical current is used to cause ions of a soluble medicament to move across the surface of the skin and to diffuse into underlying tissue. The surface of the skin is not broken by this administration of the medicament. When conducted within appropriate parameters, the sensations experienced by a subject during the delivery of the medicament in this manner are not unpleasant. Therefore, active iontophoresis presents an attractive alternative to hypodermic injections and to intravascular catheterization.

The direct current employed in active iontophoresis systems may be obtained from a variety of electrical power sources. These include consumable and rechargeable batteries, paired regions of contrasting galvanic materials that when coupled by a fluid medium produce minute electrical currents, and electrical equipment that ultimately receives power from a wall socket. The later in particular are of such bulk, weight, and cost as to necessitate being configured as items of equipment distinct from the electrical contacts that are applied directly to the skin in administering a medicament iontophoretically. Accordingly, such power sources limit the mobility of the patient during the time that treatment is in progress.

A flow of electrical current requires an uninterrupted, electrically-conductive pathway from the positive pole of a power source to the other, negative pole thereof. Living tissue is made up primarily of fluid and is, therefore, a conductor of electrical current. In an iontophoretic circuit, the opposite poles of a power source are electrically coupled to respective, separated contact locations on the skin of the subject. The difference in electrical potential created by the power source between those contact locations causes a movement of electrons and electrically charged molecules, or ions, through the tissue between the contact locations.

In an active iontophoretic delivery system, the polarity of the net overall electrical charge on dissolved molecules of a medicament determines the nature of the electrical interconnection that must be effected between the power source that is used to drive the system and the supply of medicament that is positioned on the skin of the patient at one of the contact locations to be used by the system. A positively charged medicament in a reservoir against the skin of a patient is coupled to the positive pole of the power source that is to be used to administer the medicament iontophoretically. Correspondingly, a reservoir on the skin of a patient containing a negatively charged medicament must be coupled to the negative pole of such a power source. Examples of common iontophoretically administrable medicaments in each category of polarity are listed in the table below.

| Positive Polarity Medicaments | Negative Polarity Medicaments |
|---|---|
| Bupivacaine hydrochloride | Acetic acid |
| Calcium chloride | Betamethasone sodium phosphate |
| Lidocaine hydrochloride | Copper sulfate |
| Zinc chloride | Dexamethasone sodium phosphate |
| Lidocaine | Fentinol |
| | Magnesium sulfate |
| | Naproxen sodium |
| | Sodium chloride |
| | Sodium salicylate |
| | Ascorbic acid |
| | Hydroquinone |
| | Vitamins A, C, D, or E |

The medicament is housed in a fluid reservoir, or medicament, which is then positioned electrically conductively engaging the skin of the subject at an anatomical location overlying the tissue to which the medicament is to be administered. The medicament matrix can take the form of a gel suspension of the medicament or of a pad of an absorbent material, such as gauze or cotton, which is saturated with fluid containing the medicament. In some instances the fluid containing the medicament is provided from the manufacturer in the absorbent pad. More commonly, the fluid is added to the absorbent pad by a medical practitioner at the time that the medicament is about to be administered to a subject.

An iontophoretic circuit for driving the medicament through the unbroken skin is established by coupling the appropriate pole of the power source through the medicament matrix to the skin of the subject at the anatomical location at which the medicament is to be administered. Simultaneously, the other pole of the power source is coupled to an anatomical location on the skin of the subject that is distanced from the medicament matrix. The coupling of each pole of the power source is effected by the electrical connection of each pole to a respective electrode. The electrode at the medicament matrix is referred to as an active electrode; the electrode at the contact location on the skin distanced from the medicament matrix is referred to as a return electrode.

The medicament matrix with an associated active electrode may be conveniently retained against the skin by a first adhesive patch, while the return electrode may be retained against the skin at some distance from the medicament matrix using a distinct second adhesive patch. Alternatively, the medicament matrix with the associated active electrode, as well as the return electrode, may be carried on a single adhesive patch at, respective, electrically isolated locations.

The use, of iontophoresis to administer medicaments to a subject is advantageous in several respects.

Medications delivered by an active iontophoretic system bypass the digestive system. This reduces digestive tract irritation. In many cases, medicaments administered orally are less potent than if administered transcutaneously. In compensation, it is often necessary in achieving a target effective dosage level to administer orally larger quantities of medicament than would be administered transcutaneously.

Active iontophoretic systems do not require intensive skin site sanitation to avoid infections. Patches and the other equipment used in active iontophoresis do not interact with bodily fluids and, accordingly, need not be disposed as hazardous biological materials following use. Being a noninvasive procedure, the administration of medicament using an active iontophoretic system does not cause tissue injury of the types observed with hypodermic injections and with intravenous catheterizations. Repeated needle punctures in a single anatomical region, or long term catheter residence, can adversely affect the health of surrounding tissue. Needle punctures and catheter implantations inherently involve the experience of some degree of pain. These unintended consequences of invasive transcutaneous medicament administration are particularly undesirable in an area of the body that, being already injured, is to be treated directly for that injury with a medicament. Such might be the case, for example, in the treatment of a strained muscle or tendon.

With some exceptions, no pharmacologically significant portion of a medicament delivered iontophoretically becomes systemically distributed. Rather, a medicament delivered iontophoretically remains localized in the tissue at the site of administration. This minimizes unwanted systemic side effects, reduces required dosages, and lightens the burdens imposed on the liver and kidneys in metabolizing the medicament.

The dosage of a medicament delivered iontophoretically is conveniently and accurately measured by monitoring the amount and the duration of the current flowing during the administration. With current being measured in amperes and time being measured in minutes, the dosage of medicament given transcutaneously is given in units of ampere-minutes. Due to the minute quantities of medicament required in active iontophoresis, medicament dosage in active iontophoresis is generally prescribed in milliamp-minutes. Dosage measured in this manner is more precise than is dosage measured as a fluid volume or as a numbers of tablets.

Finally, the successful operation of an active iontophoretic system is not reliant in any significant respect on the medical skills of nurses or doctors. Foregoing the involvement of such medical personnel in the administration of medicaments, whenever appropriate, favors the convenience of patients and reduces the costs associated with the delivery of such types of therapy.

SUMMARY OF THE INVENTION

The present invention promotes the wide use of active iontophoretic systems by providing improved components and combinations of components for active iontophoretic systems. The present invention thus improves the safety of patients and reduces the technical difficulty of related tasks that must by performed by medical personnel.

The teachings of the present invention enhance the reliability and the user friendliness of active iontophoretic systems and lead to reductions in the costs associated with the manufacture of such systems, as well as with the use of such systems to deliver medication.

While selected aspects of the present invention have applicability in all types of active iontophoretic systems, including those that employ plural disposable adhesive patches in combination with reusable power sources and controls, the teachings of the present invention are most optimally applicable to such system as involve a single fully-integrated, active transdermal medicament patch.

Thus, in one aspect of the present invention, a fully-integrated, independently accurately performing adhesive active transdermal medicament patch is provided.

The present invention contemplates related methods of design and manufacture, as well as methods pertaining to the treatment of patient health problems.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

BRIEF DESCRIPTION OF THE DRAWINGS

The manner in which the above-recited and other advantages and objects of the invention are obtained will be understood by a more particular description of the invention rendered by reference to specific embodiments thereof that are illustrated in the appended drawings. These figures are intended to be illustrative, not limiting. Although the invention is generally described in the context of these embodiments, it should be understood that by so doing, no intention exists to limit the scope of the invention to those particular embodiments.

Understanding that these drawings depict only typical embodiments of the invention and are not therefore to be considered limiting of scope, the invention will be described and explained with additional specificity and detail through the use of the accompanying drawings in which:

FIG. 3A is a perspective view of the active transdermal medicament patch of FIG. 1 taken from the side thereof visible in FIG. 1, the side opposite that illustrated in FIGS. 2A-2C;

FIG. 3B is an exploded perspective view of the active transdermal medicament patch of FIG. 3A showing the cover of the medicament patch, the upper face of the substrate of the medicament patch, and a circuit board sandwiched therebetween in a folded, compact state;

DETAILED DESCRIPTION OF THE INVENTION

In the following description, for purpose of explanation, specific details are set forth in order to provide an understanding of the invention. Nonetheless, the present invention may be practiced without some or all of these details. The embodiments of the present invention, some of which are described below, may be incorporated into a number of elements of medical systems additional to the medical systems in which those embodiments are by way of necessity illustrated herein. Structures and devices shown in the figures illustrate merely exemplary embodiments of the present invention, thereby to facilitate discussion of teachings of the present invention. Thus, the details of the structures and devices shown in the figures are not supplied herein in order to serve detractors as instruments with which to mount colorable denials of the existence of broad teachings of present invention that are manifest from this specification taken as a whole.

Connections between components illustrated in the figures are not limited to direct connections between those components. Rather, connections between such components may be modified, reformatted, or otherwise changed to include intermediary components without departing from the teachings of the present invention.

References in the specification to "one embodiment" or to "an embodiment" mean that a particular feature, structure, characteristic, or function described in connection with the embodiment being discussed is included in at least one embodiment of the present invention. Furthermore, the use of the phrase "in one embodiment" in various places throughout the specification is not necessarily a reference in each instance of use to any single embodiment of the present invention.

Figure 1:
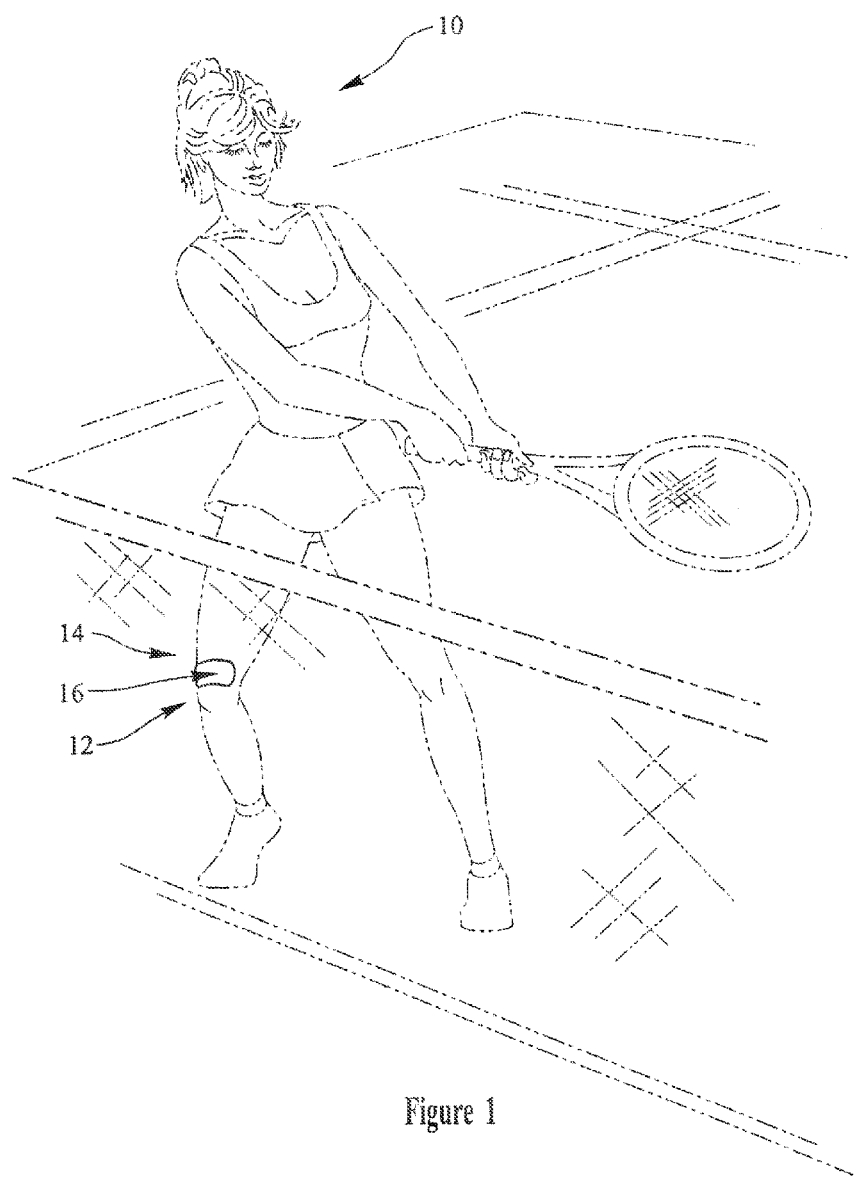
FIG. 1 is a perspective view of an embodiment of a fully-integrated, active transdermal medicament patch incorporating teachings of the present invention being worn during activity by a patient requiring the localized administration of a medicament.

FIG. 1 shows a patient 10 requiring the localized administration of a medicament to knee 12 thereof. For that purpose, patient 10 is wearing on knee 12 thereof one embodiment of an active iontophoretic delivery system 14 that incorporates teachings of the present invention. While so doing, patient 10 is nonetheless able to engage in vigorous physical activity, because delivery system 14 is entirely self-contained, and not supplied with power from any immobile or cumbersome power source. Delivery system 14 takes the form of a fully-integrated, active transdermal medicament patch 16 that is removable adhered to the skin of knee 12 of patient 10 for the duration of a predetermined therapy period. The length of the therapy period during which medicament patch 16 must be worn is determined by the rate at which medicament patch 16 delivers medicament through the skin of patient 10 and the total dose of medicament that is to be administered.

FIGS. 2A-4 taken together afford an understanding of the relationships existing among the structural elements of medicament patch 16.

Figure 2A:
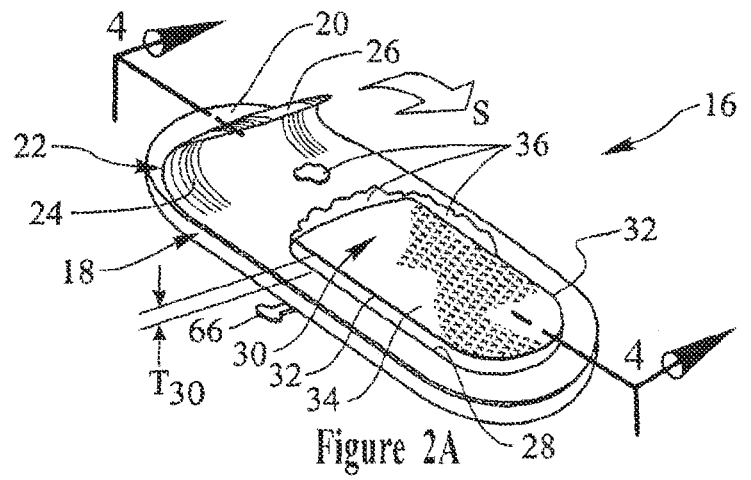
FIG. 2A is a perspective view of the active transdermal medicament patch of FIG. 1 showing the substrate of the patch, a moistened medicament matrix mounted on the therapeutic face of the substrate that engages the skin of the patient in FIG. 1, and a release liner in the process of being peeled from an adhesive coating on the portion of the therapeutic face not occupied by the medicament matrix.
Figure 2B:
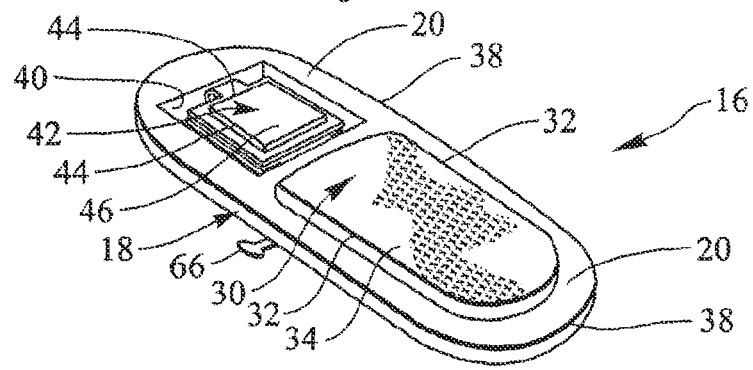
FIG. 2B is a perspective view of the active transdermal medicament patch of FIG. 2A with the release liner illustrated in FIG. 2A fully removed.
Figure 2C:
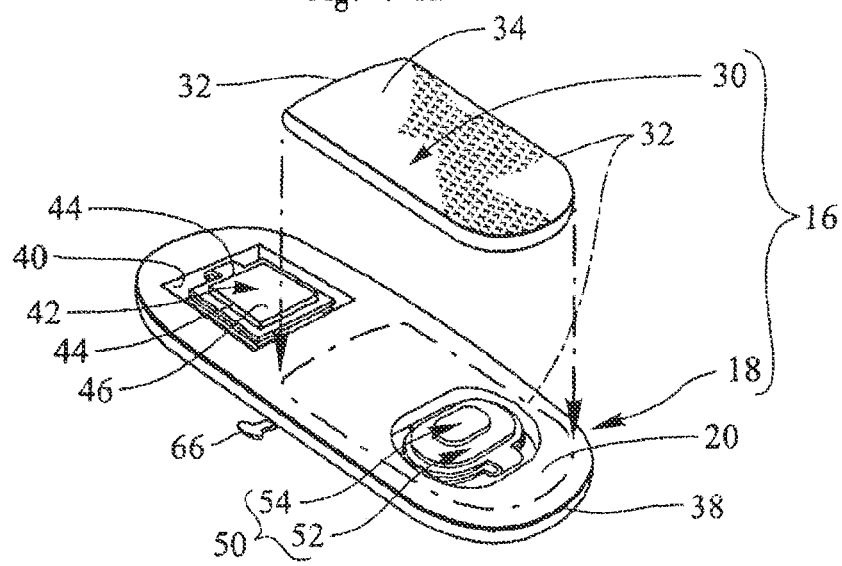
FIG. 2C is a partially-exploded perspective view of the active transdermal medicament patch of FIG. 2B that reveals the entirety of the therapeutic face of the substrate of the medicament patch.

FIGS. 2A-2C are views in various stages of disassembly of the side of medicament patch 16 that engages the skin of patient 10 in FIG. 1. FIGS. 3A-3D are similar views of the opposite side of medicament patch 16, the side thereof visible in FIG. 1. FIG. 4 is a cross-sectional elevation view of medicament patch 16 taken along section line 4-4 in FIG. 2A.

FIG. 2A reveals that medicament patch 16 includes a flexible, planar electrically non-conductive biocompatible substrate 18 having a therapeutic face 20 on one side thereof that is intended to be disposed in contact with the skin of a patient, such as patient 10 in FIG. 1. Therapeutic face 20 is coated with a biocompatible adhesive to a sufficient extent as will enable therapeutic face 20 to be removably secured to the skin of patient 10. Prior to the actual use of medicament patch 16, the adhesive on therapeutic face 20 is shielded by a removable release liner 22. As suggested by arrow S in FIG. 2A, release liner 22 is in the process of being peeled from therapeutic face 20. Release liner 22 has on the opposite sides thereof, respectively, first an exposed face 24 and second a contact face 26 that actually engages the adhesive on therapeutic face 20 of substrate 18.

Formed generally centrally through release liner 22 is a medicament matrix aperture 28. As shown in FIG. 2A, medicament matrix aperture 28 is substantially filled by a generally planar medicament matrix 30 that exhibits a periphery 32 that closely conforms in shape and size to the shape and size of medicament matrix aperture 28. Medicament matrix 30 can take the form of a gel suspension permeated by medicament, but as illustrated in FIG. 2A, medicament matrix 30 is an absorbent pad of gauze or cotton that is saturated by a user with a fluid solution containing the medicament just prior to the use of medicament patch 16. In some instances, medicament patch 16 is supplied by the manufacturer with medicament solution already permeating medicament matrix 30.

The side of medicament matrix 30 visible in FIG. 2A has a periphery 32 that encloses a skin contact surface 34 of medicament matrix 30. Medicament matrix 30 projects through medicament matrix aperture 28 in such a manner that skin contact surface 34, while oriented generally parallel to the plane of release liner 22 and the plane of therapeutic face 20 of substrate 18, is separated from each by a distance that is approximately equal to the thickness $T_{30}$ of medicament matrix 30. Skin contact surface 34 of medicament matrix 30 electrically conductively engage the skin of patient 10, when therapeutic face 20 of substrate 18 is disposed against and removably adhered thereto.

By way of example, the embodiment of medicament matrix 30 shown in FIG. 2A is an absorbent pad that must become permeated by a medicament solution before use. The saturation of medicament matrix 30 with medicament solution 36 is a process intended to be performed by medical personnel just prior to the disposition of medicament patch 16 against the skin of a patient.

FIG. 2A reveals that in such a process, drops of a medicament solution 36 may inadvertently be deposited on exposed face 24 of release liner 22 remote from medicament matrix 30. Also, at various locations about periphery 32 of medicament matrix 30, further drops of medicament solution 36 may be expected to overflow onto exposed face 24 of release liner 22 due to an over-saturation of portions of medicament matrix 30 with medicament solution 36. Such drops of medicament solution 36 do not, however, contact the adhesive on therapeutic face 20 of substrate 18. Instead, the drops of medicament solution 36 rest upon release liner 22 and are removed from medicament patch 16 with release liner 22, when release liner 22 is pealed from therapeutic face 20 of substrate 18 in the manner suggested by arrow S.

FIG. 2B shows therapeutic face 20 of medicament patch 16 after the complete removal of release liner 22 therefrom. There it can bee seen that therapeutic face 20 of medicament patch 16 has a periphery 38 and that medicament matrix 30 is positioned on therapeutic face 20 at one end of substrate 18 interior of periphery 38. Formed through the opposite end of substrate 18 at a position separated from medicament matrix 30 is a first electrode aperture 40. The size and shape of each of substrate 18, medicament matrix 30, and first electrode aperture 40 can vary from those depicted without departing from teachings of the present invention.

Accessible from therapeutic face 20 through first electrode aperture 40 is a planar first electrode, a return electrode 42 of medicament patch 16. Return electrode 42 has a periphery 44 and, interior thereof on the side of return electrode 42 visible in FIG. 2B, a skin contact surface 46. While possible to do so, return electrode 42 is not secured directly to therapeutic face 20 of substrate 18 in the manner of medicament matrix 30. Instead, return electrode 42 is maintained in a fixed relationship to other features of medicament patch 16 with the plane of skin contact surface 46 of return electrode 42 parallel to and closely coincident with the plane of therapeutic face 20. Consequently, a first electrode, such as return electrode 42, will routinely be characterized herein as being carried or positioned on therapeutic face 20, and thereby being located on the same side of substrate 18 as medicament matrix 30.

Return electrode 42 is separated from medicament matrix 30, and thus electrically isolated therefrom. Skin contact surface 46 of return electrode 42 electrically conductively engages the skin of patient 10, when therapeutic face 20 of substrate 16 is disposed against and removable adhered thereto. Accordingly, when medicament patch 16 is adhered to the skin of patient 10 as shown in FIG. 1, return electrode 42 engages the skin of patient 10 at a location that is remote from the location engaged by medicament matrix 30.

FIG. 2C is a partially-exploded perspective view of medicament patch 16 of FIG. 2B. Medicament matrix 30 is depicted above and separated from therapeutic face 20 of substrate 18. Revealed thereby is a second electrode aperture 48 that is formed through substrate 18 at a position separated from first electrode aperture 40 and, correspondingly, also from return electrode 42. Superimposed by way of reference in phantom on therapeutic face 20 is periphery 32 of medicament matrix 30, which in the assembled condition of medicament patch 16 shown in FIG. 2B entirely obscures second electrode aperture 48.

Accessible from therapeutic face 20 through electrode aperture 44 is a planar second electrode, active electrode 50 of medicament patch 16. Active electrode 50 includes an electrically-conductive planar backing layer 52 and a smaller electrically-conductive planar pH-control layer 54 disposed centrally thereupon. While possible to do so, active electrode 50 is not secured directly to therapeutic face 20 of substrate 18 in the manner of medicament matrix 30. Instead, by the attachment of active electrode 50 to other structural elements of medicament patch 16, active electrode 50 is maintained in a fixed relationship to other features of medicament patch 16 with the plane of each of backing layer 52 and pH-control layer 54 parallel to and closely coincident with the plane of therapeutic face 20. Consequently, a second electrode, such as active electrode 50, will routinely be characterized herein as being carried or positioned on therapeutic face 20, and thereby being located on the same side of substrate 18 as, for example, return electrode 42 and medicament matrix 30.

In the assembled condition of medicament patch 16 shown in FIG. 2B, the side of medicament matrix 30 opposite from skin contact surface 34, which is therefore not visible in FIG. 2B, rests against and may be secured to each of backing layer 52 and pH-control layer 54 of active electrode 50. This is borne out in FIG. 2C, where pH-control layer 54 is shown carried on backing layer 52, while each of these components of active electrode 50 are located interior of periphery 32 of medicament matrix 30 as superimposed in phantom on therapeutic face 20.

FIG. 3A is a perspective view of medicament patch 16 taken from the side thereof visible in FIG. 1 when being worn by patient 10, the side of medicament patch 16 opposite that illustrated' in FIGS. 2A-2C. The side of medicament patch 16 shown in FIG. 3A is encased in a protective cover 56 that is, but need not be, coextensive with substrate 18 of medicament patch 16. By way of example, cover 56 is depicted as being opaque and as including as the sole transparent portion thereof a small observation port 58. Consequently, features of medicament patch 16 beneath cover 56, such as first electrode aperture 40 and second electrode aperture 48, are shown in dashed lines.

Also included in dashed lines in FIG. 3A are some components of medicament patch 16 that are carried on substrate 18 beneath cover 56. These include electronic circuitry 60, a power source 62, and a switch 64. Switch 64 is depicted by way of example as a user-operated pull tab switch that permits the initiation of the operation of power source 62 by withdrawing an activation stem 66 of switch 64 from between cover 56 and substrate 18 in a manner suggested by arrow P. Electronic circuitry 60 is surmounted by a light-emitting diode 67 or other visual indicator that communicates to a user information about the operative status of medicament patch 16. Light-emitting diode 67 is therefore located beneath and in alignment with observation port 58 in cover 56.

Electronic circuitry 60, power source 62, and switch 64 are not mounted directly to substrate 18, although any or all of these components of medicament patch 16 may be secured directly to substrate 18, or recessed in whole or in part into substrate 18. Instead, electronic circuitry 60, power source 62, and switch 64 are maintained in a fixed relationship to each other by being commonly secured to a circuit board 68. Circuit board 68 directly engages substrate 18 beneath cover 56, indirectly fixing each of electronic circuitry 60, power source 62, and switch 64 relative to each other and to other features of medicament patch 16.

Figure 3C:
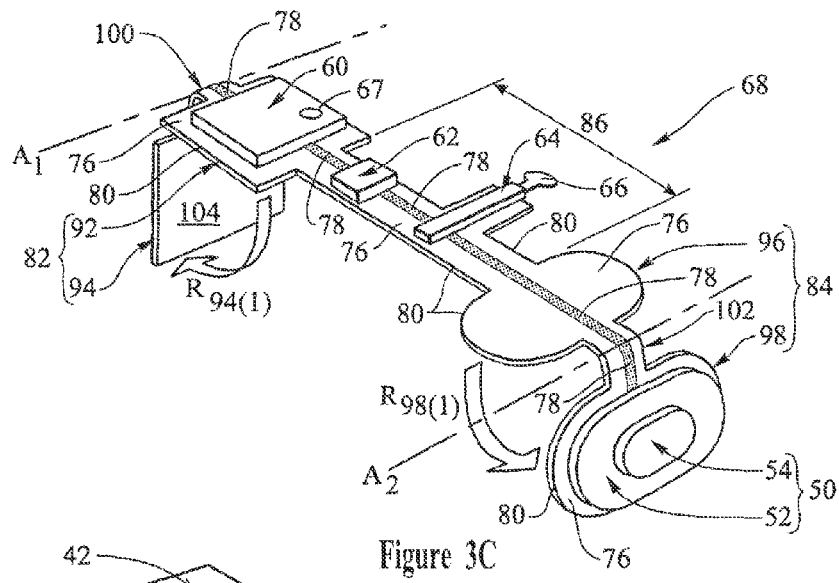
FIG. 3C is a perspective view of the circuit board of FIG. 3B in a partially-unfolded state thereof.
Figure 3D:
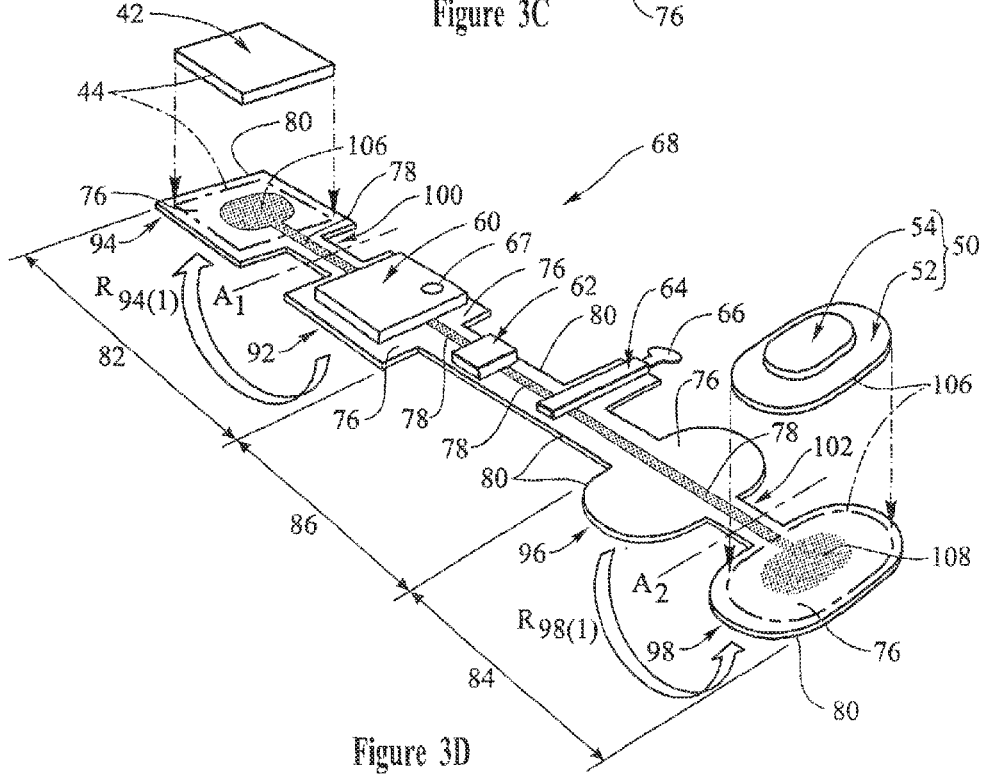
FIG. 3D is a partially-exploded perspective view of the circuit board of FIG. 3C in a fully-unfolded, planar state thereof.
Figure 4:
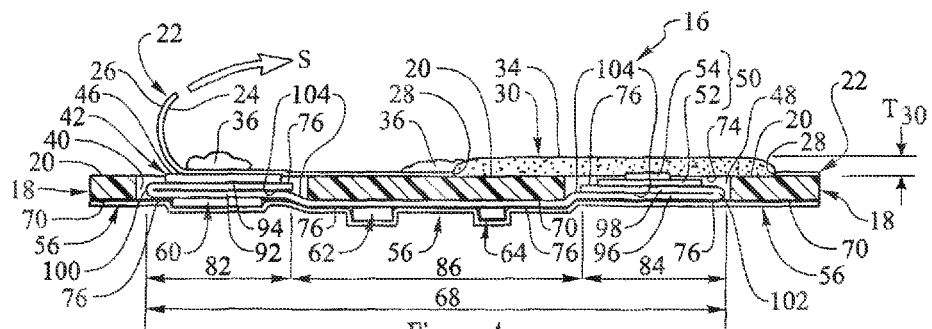
FIG. 4 is a cross-sectional elevation view of the active transdermal medicament patch of FIG. 2A taken along section line 4-4 shown therein.

Circuit board 68 will be explored in greater detail in FIGS. 3B-3D.

FIG. 3B is an exploded perspective view of medicament patch 16 of FIG. 3A. Cover 56 is depicted above and separated from substrate 18. Revealed thereby is an upper face 70 of substrate 18. Upper face 70 has a periphery 72 that is substantially similar in size and shape to periphery 38 of therapeutic face 20 of substrate 18 shown in FIGS. 2B and 2C on the opposite side of substrate 18 from upper face 70. First electrode aperture 40 and second electrode aperture 48 are formed through substrate 18 at spaced-apart locations. Visible through second electrode aperture 48 is medicament matrix 30 and a portion of a securement surface 74 thereof. Medicament matrix 30 closes the side of second electrode aperture 48 that opens onto therapeutic face 20 of substrate 18. This is the situation when securement surface 74 of medicament matrix 30 engages therapeutic face 20 as shown in FIG. 2B and as suggested in FIG. 2C by the rendering in phantom on therapeutic face 20 of periphery 32 of medicament matrix 30.

Sandwiched between cover 56 and upper face 70 of substrate 18 is circuit board 68. On the side of circuit board 68 visible in FIG. 3B is a portion of a support face 76 thereof upon which are carried electronic circuitry 60, power source 62, and switch 64. These and other electrical circuit elements of medicament matrix 30 are electrically interconnected by an electrically-conductive printed circuit 78 that is applied to support face 76, usually before other electrical circuit elements are mounted on circuit board 68. The depiction of printed circuit 78 in FIG. 3B and thereafter herein is entirely schematic and is not intended to reveal any details about the layout particulars of printed circuit 78.

Power source 62 is, by way of example, a miniature battery of about 3 volts potential. The current supplied by power source 34 to electronic circuitry 60 is thus non-alternating. Power source 62 may be a battery of higher or lower output potential, or power source 62 may be a plurality of series-connected batteries of equal or unequal output potential. Accordingly, for most medical applications, the output voltage produced by power source 62 ranges from about 1.00 volt to about 15.00 volts. Alternatively, the output voltage produced by power source 62 ranges from about 2.00 volts to about 9.00 volts, or from about 3.00 volts to about 6.00 volts.

In general, the greater the output voltage produced by a mobile power source, such as power source 62 associated with an active transdermal medicament patch, the larger will be the skin current $I_S$ produced by that medicament patch, and the shorter will be the therapy period required to enable that medicament patch to administer any predetermined total dosage $D_T$ of medicament. While such a result is salutary relative to minimizing the time during which a patient is required to be encumbered by wearing the medicament patch, the larger the skin current $I_S$ produced by a medicament patch, the greater the likelihood that a wearer of the medicament patch will experience uncomfortable sensations, or even pain, during therapy. Accordingly, an unavoidable tradeoff exists between the desirable ends of comfort and of speedy therapy. Lower levels of power source output, such as those endorsed by teachings of the present invention, are calculated to increase patient comfort and to improve the likelihood that a patient will be willing to successfully complete a prescribed course of therapy, once that course of therapy has been undertaken.

Support face 76 of circuit board 68 has a complex periphery 80 that assumes an irregular, asymmetrical barbell-shape. Alternative configurations in circuit board 68 would not depart from the teachings of the present invention. At a first end 82 of circuit board 68 located in proximity to first electrode aperture 40, periphery 80 of support face 76 is similar in shape, but smaller in extent than first electrode aperture 40. At a second end 84 of circuit board 68 located in proximity to second electrode aperture 44, periphery 80 of support face 76 is similar in shape, but smaller in extent than second electrode aperture 48. Interconnecting first end 82 and second end 84 of circuit board 68 is an intermediate portion 86 of circuit board 68 in which periphery 80 of support face 76 is made up of linear segments.

Electronic circuitry 60 is mounted on support face 76 at first end 82 of circuit board 68. Power source 62 and switch 64 are mounted on support face 74 of intermediate portion 86 of circuit board 68. Support face 76 at first end 82 of circuit board 68 is shown as being free of electrical circuit elements, other than printed circuit 78. The positions of such electrical circuit elements of medicament patch 16 may be altered without departing from the teachings of the present invention.

Superimposed by way of reference in phantom on upper face 70 of substrate 18 is periphery 80 of intermediate portion 86 of circuit board 68. In the assembled condition of medicament patch 16 shown in FIG. 3A, intermediate portion 86 extends longitudinally along substrate 18 between first electrode aperture 40 and second electrode aperture 48 and laterally thereof to a linear portion 90 of periphery 72 of upper face 70 of substrate 18. On upper face 70 of substrate 18, the phantom representation of intermediate portion 86 defines a circuit board contact area 88. In circuit board contact area 88 the side of circuit board 68 not visible in FIG. 3B engages and may thus be secured, as with adhesive, to upper face 70 of substrate 18.

Circuit board 68 is manufactured from an electrically-nonconductive material. Depending on the absolute size of circuit board 68 and the relative size of circuit board 68 to the size of substrate 18, the material from which circuit board 68 is fabricated can be rigid or minimally flexible. In the assembled condition of medicament patch 16, however, rigidity in circuit board 68 preferably does not prevent medicament patch 16 from being able to conform to curving skin surfaces at locations on the person of patient at which iontophoretic therapy is to be provided. The embodiment of circuit board 68 shown in FIG. 3B is manufactured from thin sheeting, such as sheeting made from a flexible polyester film, such as Mylar® brand polyester film manufactures by DuPont Teijin Films U.S. Ltd. of Hopewell, Va., U.S.A. As a result, circuit board 68 is relatively insubstantial and highly flexible.

Intermediate portion 86 of circuit board 68 includes a single layer of circuit board material. By contrast, as revealed in the enlarged portion of periphery 80 of support face 76 of first end 82 of circuit board 68 included in FIG. 3B, first end 82 of circuit board 68 includes a primary layer 92 above a substantially congruent secondary layer 94. Primary layer 92 of first end 82 of circuit board 68 carries electronic circuitry 60 and is a coplanar extension of intermediate portion 86. Similarly, as revealed in the enlarged portion of periphery 80 of support face 76 of second end 84 of circuit board 68 included in FIG. 3B, second end 84 of circuit board 68 includes a primary layer 96 above a substantially congruent secondary layer 98. Primary layer 96 of second end 84 of circuit board 68 carries a portion of printed circuit 78 and is also a coplanar extension of intermediate portion 86.

FIG. 3C is a perspective view of circuit board 68 of FIG. 3B. As indicated by arrow $R_{94(1)}$ in FIG. 3C, secondary layer 94 of first end 82 of circuit board 68 has been rotated by 90 degrees in a clockwise direction out of the position thereof shown in FIG. 3B about a first axis $A_1$ located between secondary layer 94 and primary layer 92 of circuit board 68. In a somewhat similar manner, as indicated by arrow $R_{98(1)}$ in FIG. 3C, secondary layer 98 of second end 84 of circuit board 68 has been rotated by 90 degrees in a counter clockwise direction out of the position thereof shown in FIG. 3B about a second axis $A_2$ located between secondary layer 98 and primary layer 96 of circuit board 68. First axis $A_1$ and second axis $A_2$ are generally parallel to one another and perpendicular to the longitudinal extent of circuit board 68 at the opposite ends thereof. Variations in such relationships would not be contrary to teachings of the present invention, as first axis $A_1$ and second axis $A_2$ can with substantially equivalent efficacy be intersecting relative to each other, or be individually or jointly located to one side or on opposite sides of the longitudinal extent of a circuit board, such as circuit board 68.

The partial disassembly of circuit board 68 depicted in FIG. 3C reveals that at first axis $A_1$, primary layer 92 and secondary layer 94 of first end 82 of circuit board 68 are connected by a bendable first electrode hinge 100. Similarly, at second axis $A_2$, primary layer 96 and secondary layer 98 of second end 84 of circuit board 68 are connected by a bendable second electrode hinge 102.

Either or both of first electrode hinge 100 and second electrode hinge 102 may be structures distinct from the portions of circuit board 68 interconnected thereby. In such an embodiment of a circuit board incorporating teachings of the present invention, one or both of secondary layer 94 and secondary layer 98 would be manufactured as distinct articles and then interconnected during further manufacturing activities by a corresponding one or both of first electrode hinge 100 and second electrode hinge 102. This could be a desirable arrangement, where the material of circuit board 68 is rigid or only partially flexible. Then, secondary layer 94, secondary layer 98, and the central portion of circuit board 68 between first axis $A_1$ and second axis $A_2$ could be manufactured from such a rigid or only partially flexible material and subsequently interconnected by flexible or mechanically bendable hinges, such as first electrode hinge 100 and second electrode hinge 102.

In the embodiment of circuit board 68 illustrated, however, first electrode hinge 100 and second electrode hinge 102 are coplanar extension of the portions of circuit board 68 interconnected thereby. The required capacity for bending in first electrode hinge 100 and second electrode hinge 102 arises from the flexibility of the material of which circuit board 68 is manufactured. Were that material rigid or only partially flexible, the degree of bendability required in first electrode hinge 100 and second electrode hinge 102 can be achieved without departing from teachings of the present invention by thinning or scoring the side of each of first electrode hinge 100 and second electrode hinge 102 that is not visible in FIG. 3C.

Thus, support face 76 of circuit board 68 extends in a continuous manner across first electrode hinge 100 to secondary layer 94 of first end 82 and across second electrode hinge 102 to secondary layer 98 of second end 84. Active electrode 50 can be appreciated from FIG. 3C to be carried on a portion of support face 76 that extends onto secondary layer 98 of second end 84 of circuit board 68 and to be electrically coupled to other electrical circuit elements of medicament patch 16 by the portion of printed circuit 78 that traverses second electrode hinge 102.

Correspondingly, the side of circuit board 68 opposite from support face 76 thereof is a continuous surface that may, if convenient, remain entirely free of electrical circuit elements. A portion of such a continuous attachment face 104 of circuit board 68 is visible on the side of secondary layer 94 of first end 82 of circuit board 68 presented in FIG. 3C. In the folded, compact state of circuit board 68 depicted earlier in FIG. 3C, attachment face 104 on secondary layer 94 of first end 82 of circuit board 68 engages attachment face 104 on primary layer 92 of first end 82, while attachment face 104 on secondary layer 98 of second end 84 engages attachment face 104 on primary layer 96 of second end 84. These relationships are depicted explicitly subsequently in FIG. 4.

FIG. 3D is a perspective view of circuit board 68 of FIG. 3C. As indicated by arrow $R_{94(2)}$ in FIG. 3D, secondary layer 94 of first end 82 of circuit board 68 has been rotated by an additional 90 degrees in a clockwise direction out of the position thereof shown in FIG. 3C about first axis $A_1$. As indicated by arrow $R_{98(2)}$ in FIG. 3D, secondary layer 98 of second end 84 of circuit board 68 has been rotated by an additional 90 degrees in a counter clockwise direction out of the position thereof shown in FIG. 3C about a second axis $A_2$. Thus, depicted in FIG. 3D is the fully unfolded, planar state of circuit board 68.

In view of the sequence of views of circuit board 68 presented in FIGS. 3B-3D, it is apparent that in one aspect of the present invention an active transdermal medicament patch employing a circuit board having mounted on an attachment face thereof a power source and an electrode, such as return electrode 42 or active electrode 50, is provided with electrode flexion means that traverses the circuit board intermediate the electrode and the power source for permitting bending of the circuit board between a planar state of the circuit board and a compact state of the circuit board. In the compact state of the circuit board, a portion of the attachment face in an electrode region of the circuit board located on the same side of the electrode flexion means as the electrode engages a portion of the attachment face in a power source region of the circuit board located on the same side of the electrode flexion means as the power source.

Pursuant to such teachings, it is possible in an active transdermal medicament patch to benefit from the use of a circuit board that is in effect electrically two-sided, but that carries only on a single side thereof the electrical circuit components of the medicament patch. This leaves the other side of the circuit board free of electrical circuit components. The freedom to maintain one side of the circuit board free of electrical circuit components is an optional benefit of an electrode flexion means incorporating teachings of the present invention.

As shown by way of example in FIG. 3D relative to first electrode hinge 100, circuit board 68 includes a first electrode region corresponding to secondary layer 94 of first end 82 and a power source region corresponding to the portion of circuit board 68 on the same side of first axis $A_1$ as power source 62. First electrode hinge 100 traverses circuit board 68 between return electrode 42 and power source 62 and permits circuit board 68 to bend out of the planar state thereof shown in FIG. 3D and into a more compact state thereof shown in FIG. 3B. In the compact state of circuit board 68, attachment face 104 on secondary layer 94 of first end 82 of circuit board 68 engages attachment face 104 on primary layer 92.

As shown by way of example in FIG. 3D relative to second electrode hinge 102, circuit board 68 includes a second electrode region corresponding to secondary layer 98 of second end 84 and a power source region corresponding to the portion of circuit board 68 on the same side of second axis $A_2$ as power source 62. Second electrode hinge 102 traverses circuit board 68 between active electrode 50 and power source 62 and permits circuit board 68 to bend out of the planar state thereof shown in FIG. 3D and into a more compact state thereof shown in FIG. 3B. In the compact state of circuit board 68, attachment face 104 on secondary layer 98 of first end 84 of circuit board 68 engages attachment face 104 on primary layer 96.

In FIG. 3D, return electrode 42 is depicted above and separated from support face 76 of circuit board 68. Revealed thereby is a return electrode contact pad 106 in which printed circuit 78 terminates on secondary layer 94 of first end 82 of circuit board 68. Superimposed by way of reference in phantom on support face 76 is periphery 44 of return electrode 42, which in the assembled condition of medicament patch 16 shown in FIG. 2B entirely obscures return electrode contact pad 106.

Active electrode 50 is depicted in FIG. 3D above and separated from support face 76 of circuit board 68. Revealed thereby is an active electrode contact pad 108 in which printed circuit 78 terminates on secondary layer 98 of second end 84 of circuit board 68. Superimposed by way of reference in phantom on support face 76 is periphery 106 of backing layer 52 of active electrode 50, which in the assembled condition of medicament patch 16 shown in FIG. 2B entirely obscures active electrode contact pad 108.

FIG. 4 is a cross-sectional elevation view of medicament patch 16 taken along section line 4-4 in FIG. 2A. As a result, FIG. 4 depicts in edge view both sides of substrate 18, as well as the interaction by way of first electrode aperture 40 and second electrode aperture 48 of other elements of medicament patch 16 discussed previously. In particular, circuit board 68 is shown in the fully folded, compact state thereof carrying electrical circuit components. From among the electrical circuit components carried on circuit board 68, printed circuit 78 been omitted out of convenience due to the thinness thereof. Nonetheless, the entirety of printed circuit 78 is disposed as shown in FIG. 3D, on support face 76 along with the balance of the electrical circuit elements of medicament patch 16.

As suggested by arrow S in FIG. 4, release liner 22 is in the process of being peeled from therapeutic face 20 of substrate 18, thereby to free the adhesive coating on therapeutic face 20 for the releasable attachment of medicament patch 16 to the skin of a patient. Simultaneously, the detachment of release liner 22 from medicament patch 16 will result in the removal of stray droplets of medicament solution 36. Securement surface 74 of medicament matrix 30 engages pH-control layer 54 and backing layer 52 of active electrode 50 interior of second electrode aperture 48. In second end 84 of circuit board 68, attachment face 104 of secondary layer 98 engages attachment face 104 of primary layer 96. Electronic circuitry 60, power source 62, and switch 64 are carried on support face 76 of circuit board 68 and sealed therewith against upper face 70 of substrate 18 by cover 56. In first end 82 of circuit board 68, attachment face 104 of secondary layer 94 engages attachment face 104 of primary layer 92 interior of first electrode aperture 40

Figure 5A:
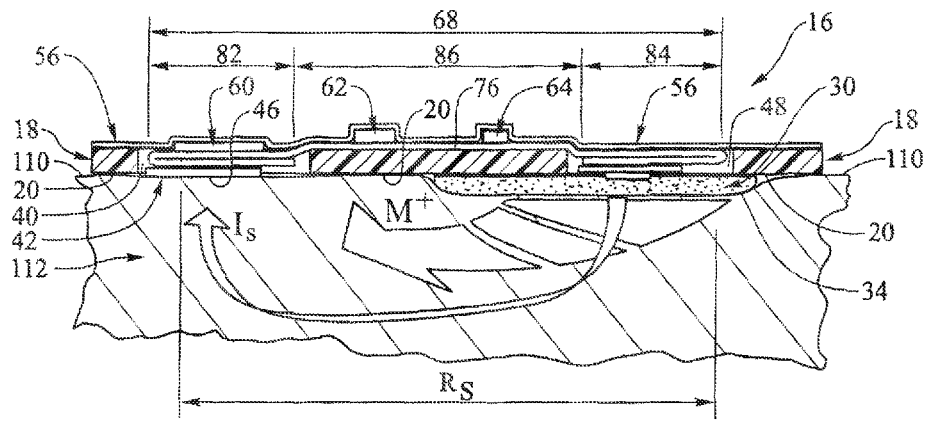
FIG. 5A is cross-sectional elevation view of the active transdermal medicament patch of FIG. 4 inverted and disposed against the skin of a patient, thereby to illustrate the movement of a medicament of positive polarity through subcutaneous tissue of the patient.
Figure 5B:
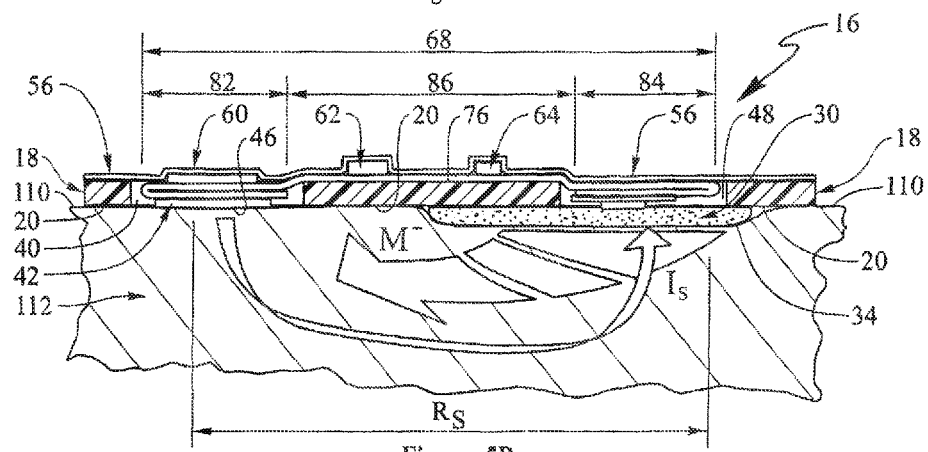
FIG. 5B is a diagram like that of FIG. 5A, illustrating the movement of a medicament of negative polarity through subcutaneous tissue of a patient.

FIGS. 5A and 5B are related diagrams that compare the movement of medicaments of differing polarities through the skin of a wearer of medicament patch 16. The alterations in electrical interconnections required among element of medicament patch 16 to produce those movements are not illustrated, but will be mentioned.

FIG. 5A illustrates the movement of molecules of a positive medicament $M^+$ that exhibits a net positive polarity. Therapeutic face 20 of substrate 18 is shown as being disposed against the surface 110 of skin 112. Then skin contact surface 34 of medicament matrix 30 and skin contact surface 46 of return electrode 42 each electrically conductively engage surface 110 of skin 112 at separated locations. Aside from the conductivity of skin 112, these locations are electrically isolated from each other. The negative pole of power source 34 is coupled directly or indirectly to return electrode 42. The positive pole of power source 62 is coupled directly or indirectly to medicament matrix 30, which engages skin 112 at a location remote from return electrode 42. The electromotive differential thusly applied to skin 112 between medicament matrix 30 and return electrode 42 induces molecules of positive medicament $M^+$ to move as positive ions out of medicament matrix 30 toward skin 112, across the unbroken surface 110 of skin 112, and through skin 112 in the direction of return electrode 42. This movement is indicated in FIG. 5A by a dashed arrow labeled $M^+$.

In electrical circuits, the flow of electrical current is conventionally indicated as a flow through the circuit from the positive to the negative pole of the power source employed therewith. Therefore, in FIG. 5A, an electrical skin current $I_S$ is schematically indicated by a solid arrow to flow through skin 112 from medicament matrix 30, which is associated with the positive pole of power source 62, to return electrode 42 associated with the negative pole of power source 62. In the use of medicament patch 16 to administer a positive medicament $M^+$, the direction of movement of molecules of positive medicament $M^+$ through skin 112 thus coincides with the direction of skin current $I_S$.

While living tissue is a conductor of electric current, living tissue does nonetheless resist the flow of electrical current therethrough. It is the function of power source 62 to apply a sufficient electromotive force differential through skin 112 between medicament matrix 30 and return electrode 42 as to overcome this resistance. The presence of electrical resistance in skin 112 is indicated schematically in FIG. 5A as skin resistance $R_S$. Skin resistance $R_S$ varies among human subjects over a wide range. Generally, within a few minutes of beginning to conduct a skin current, such as skin current $I_S$, the skin resistance $R_S$ of most subjects undergoes transient changes and stabilizes at about 10 kilo-ohms, or more broadly stabilizes in a range of from about 10 kilo-ohms to about 50 kilo-ohms.

In FIG. 5B, the transcutaneous administration is depicted of molecules of a negative medicament $M^-$ that exhibits a net negative polarity. Therapeutic face 20 of substrate 18 is shown again as being disposed against surface 110 of skin 112. Then skin contact surface 34 of medicament matrix 30 and skin contact surface 46 of return electrode 42 each electrically conductively engage surface 110 of skin 112 at separated locations. Aside from the conductivity of skin 112, these locations are electrically isolated from each other. The presence of electrical resistance in skin 112 is indicated schematically in FIG. 5B as skin resistance $R_S$.

To infuse a negative medicament M the electrical components of a medicament patch incorporating teachings of the present invention must be altered from those described above relative to FIG. 5A. Accordingly, the positive pole of power source 62 is coupled directly or indirectly to return electrode 42. Correspondingly, the negative pole of power source 62 is coupled directly or indirectly to medicament matrix 30. The electromotive differential thusly applied to skin 112 between return electrode 42 and medicament matrix 30 induces molecules of negative medicament N⁻ to move as negative ions out of medicament matrix 30 toward skin 112, across the unbroken surface 110 of skin 112, and through skin 112 in the direction of return electrode 42. This movement is indicated in FIG. 5B by a dashed arrow labeled M.

The flow of electrical current in an electrical circuit is conventionally indicated as a flow through the circuit from the positive to the negative pole of the power source employed therewith. In FIG. 5B, a skin current $I_S$ schematically indicated by a solid arrow to flow through skin 112 toward medicament matrix 30, which is associated with the negative pole of power source 62, from return electrode 42 associated with the positive pole of power source 62. In the use of medicament patch 16 to administer negative medicament M⁻, the movement of molecules of negative medicament M⁻ through skin 112 is in a direction that is opposite to that of skin current $I_S$.

For convenience and consistency in discussing various embodiments of the invention, the convention will be uniformly observed hereinafter that a negative medicament is to be administered. Nonetheless, this is not an indication that the teachings of the present invention have relevance exclusively to the administration of negative medicaments, as the present invention has applicability with equal efficacy to the administration of positive medicaments.

According to another aspect of the present invention, an active transdermal medicament patch, such as medicament patch 16 in FIGS. 1-5B, includes voltage means non-removably carried on the substrate of the medicament patch that is driven by a power source that is also carried on that substrate. The voltage means performs a pair of functions. First, the voltage means is for generating a substantially invariant voltage output during a predetermined therapy period. Second, the voltage means is for applying that substantially invariant voltage output across a medicament matrix carried on the substrate of the medicament patch and skin of a patient that is engaged by the medicament matrix. The inventive voltage means performs these functions, notwithstanding the variability inherent in the output potential of a portable power source, such as power source 62. Such a power source will exhibit a precipitous decline in output of at least 5% upon being first activated. Thereafter, the output of such a power source will decline relatively steadily in output by about 5% or more during each succeeding hour of operation.

The inclusion in a an active transdermal medicament patch, such as medicament patch 16 in FIGS. 1-5B, of a voltage means of the type described causes a substantially constant skin current $I_S$ to flow through the medicament matrix of the medicament patch and skin of a wearer of the medicament patch during the entire course of the predetermined therapy period. In this manner, the total dosage $D_T$ of medicament delivered by an active transdermal medicament patch incorporating teachings of the present invention is determinable with reasonable medical reliability by reference to the total of the time during which the medicament patch is employed for therapy.

The absolute accuracy of this manner of measuring the actual dosage of a medicament delivered by the apparatus and methods of the present invention is necessarily qualified to some degree.

At the commencement of the passage of a skin current through the skin of a patient, the resistance of the skin to the passage of electrical current is far higher than is skin resistance $R_S$ once a flow of skin current has been established. Shortly upon establishing a skin current $I_S$, skin resistance $R_S$ of most subjects undergoes gradual transient changes before stabilizing. Accordingly, for a few initial minutes of a predetermined therapy period, the amount of skin current that will flow through the skin will vary somewhat from the stable level of current subsequently observed during the balance of the therapy period. Nonetheless, over a therapy period of a few hours, this initial variation in the amount of skin current caused by transients in skin resistance $R_S$ has been determined to have a negligible effect on the overall dose of medicament ultimately administered.

Similarly, certain electrical components of the types called for in the exemplary embodiment of an inventive circuit disclosed herein as being suitable to performing the functions of an inventive voltage means are occasionally susceptible, due to heating or otherwise, of mildly transient start-up performances. These also stabilize after a relatively short fraction of any normal therapy period and produce no more than a negligible effect on the overall dose of medicament ultimately administered during that entire therapy period.

As a result, it is contemplated that any such biological or electrical transients as might be observable in commencing the administration of medicament using apparatus and methods of the present invention do not derogate from what is medically accepted to be a substantially constant flow of skin current through the medicament matrix of an associated medicament patch and the skin of a wearer of the medicament patch during the entire course of some predetermined therapy period.

Figure 6:
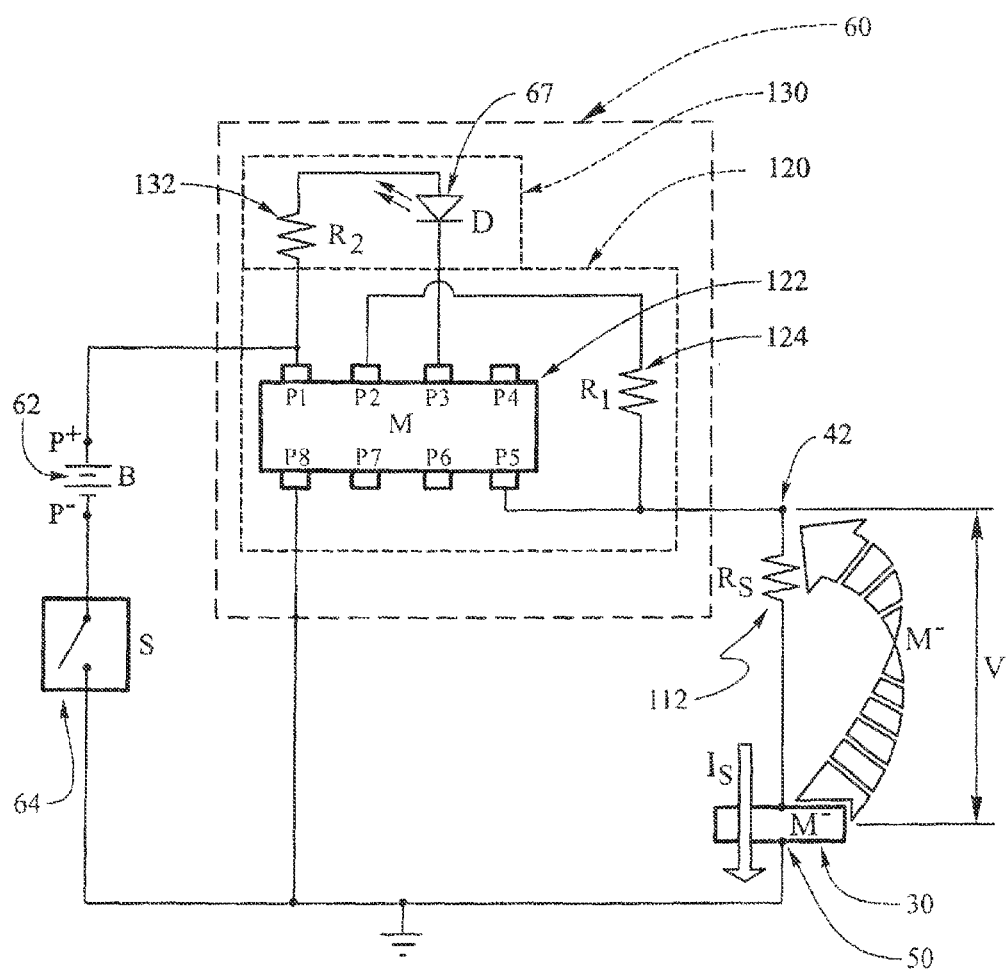
FIG. 6 is a schematic diagram of an embodiment of electronics incorporating teachings of the present invention and suitable for use in the active transdermal medicament patch of FIG. 5B.

By way of example and not limitation, shown in FIG. 6 is an embodiment of electronic circuitry 60 that is capable of performing the functions of a voltage means according to teachings of the present invention. Electronic circuitry 60 includes a voltage regulator 120, which is coupled directly to the positive pole P⁺ of power source 62. Power source 62 supplies a voltage that drives voltage regulator 120 and the other elements of electronic circuitry 60. The output of voltage regulator 120 is supplied to return electrode 42, which engages skin 112 of a patient. Together with power source 62, voltage regulator 120 causes an electrical skin current $I_S$ to flow through skin 112 from return electrode 42 in the direction shown, overcoming in the process electrical skin resistance $R_S$ of skin 112.

The negative pole P⁻ of power source 62 is coupled through switch 64 and active electrode 50 to medicament matrix 30, which engages skin 112 of a patient at a location that is remote from return electrode 42. According to the convention set forth above, medicament matrix 30 is filled with molecules of a negative medicament M⁻. As a result of the electrical potential correspondingly imposed on skin 112 between return electrode 42 and medicament matrix 30, a flow of molecules of negative medicament M⁻ is induced from medicament matrix 30, through skin 112, and toward return electrode 42 in a direction that is opposite to that of skin current $I_S$.

Voltage regulator 120 includes a programmable microprocessor 122 having contact pins P1-P8. Microprocessor 122 is a semiconductor chip that includes a read-only memory that retains data when power to microprocessor 122 is terminated, but that can be electronically erased and reprogrammed without being removed from the circuit board upon which microprocessor 122 is mounted with other electrical circuit components. Advantageously, microprocessor 122 exhibits low power consumption requirements, which are in harmony with the use of a small, non-rechargeable mobile power source, such as power source 62.

Software installed in microprocessor 122 enables various of contact pins P1-P8 to performing multiple functions. The physical size of microprocessor 122 is accordingly small as compared with a microprocessor carrying only single-use contact pins, and the physical coupling of microprocessor 122 with other electrical circuit elements of electronic circuitry 60 necessitates fewer lead attachment soldering operations than would be the case using single-use contact pins. This reduces manufacturing costs and failures, as well as contributes to a desirably small footprint in microprocessor 122.

In voltage regulator 120 contact pin P6 and contact pin P7 of microprocessor 122 are not used. Positive pole $P^+$ of power source 62 is coupled directly to contact pin P1, which therefore functions as an input contact for microprocessor 122. Contact pin P8 is grounded. The voltage output from voltage regulator 120 appears at contact pin P5 of microprocessor 122. Therefore, contact pin P5 functions as an output contact for microprocessor 12, and contact pin P5 is coupled directly to return electrode 42. To insure that the voltage appearing at contact pin P5 is a substantially invariant voltage output, a sensing resistor 124 is electrically coupled between contact pin P5 and contact pin P2, which therefore functions as a current monitoring contact for microprocessor 122.

According to yet another aspect of the present invention, an active transdermal medicament patch, such as medicament patch 16 in FIGS. 1-5B, includes activity indication means non-removably carried on the substrate of the medicament patch for communicating to a user that a voltage means as described above is operating. As shown by way of example in FIG. 6, in addition to voltage regulator 120, electronic circuitry 60 includes an indicator circuit 130. Indicator circuit 130 includes light-emitting diode 67 and a bias resistor 132 that are series-connected between contact pin P1 of microprocessor 122 and contact pin P3, which therefore functions as an activity indication contact for microprocessor 122.

Microprocessor 122 necessarily includes a driver that operates light-emitting diode 67 in any selected manner preferred by medical personal and suited to the sensory capacities of the patient with whom medicament patch 16 is to be used for therapy. For example, such a driver in microprocessor 122 might be programmed to operate light-emitting diode 67 only on an intermittent basis during any therapy period in order to conserve the capacity of power source 62 for use by other electrical elements of electronic circuitry 60.

The operation of light-emitting diode 67 by microprocessor 122 affords a visual indication that voltage regulator 120 is functioning. In the alternative, indicator circuit 130 could employ in place of light-emitting diode 67 an auditory indicator or a tactile indicator that engages skin 112 of the patient or that can be encountered at will by attending medical personnel in the manner of taking a pulse. Such a tactile indicator could, for example, be a vibrating element or a heating element. Auditory or tactile indicators may consume the output capacity of power source 62 more rapidly than a light-emitting diode, and particularly more rapidly than an intermittently-operated light-emitting diode.

The migration of medicament through skin 112 is reflected as a flow of skin current $I_S$ from contact pin P5 of microprocessor 122 to return electrode 42. The flow of skin current $I_S$ is detected at contact pin P2 of microprocessor 122, whereby microprocessor 122 is able, by integrating the flow of skin current $I_S$ over time, to monitor the running cumulative total of the amount of medicament administered. When the output of that integration function reaches some predetermined total dosage $D_T$ of medicament, microprocessor 122 is programmed to function as a circuit breaker and disable power source 62, thereby terminating skin current $I_S$ and the migration of medicament through skin 112.

Voltage regulator 120 is so configured as to cause the voltage applied through skin 112 between return electrode 42 and medicament matrix 30 to be substantially invariant for the full duration of a predetermined therapy period $T_M$ that ranges in duration from about 1 hour to about 6 hours, or more narrowly from about 2 hours to about 4 hours. Any such substantially invariant voltage applied through skin 112 between return electrode 42 and medicament matrix 30 will cause iontophoretic medicament migration to occur through skin 112 from medicament matrix 30 to return electrode 42 at a substantially constant rate.

When medicament migration occurs at a substantially constant rate, skin current $I_S$ is substantially constant, and the integration function to be performed by microprocessor 122 in monitoring the administration of total dosage $D_T$ of medicament reduces to one of using a clock in microprocessor 122 to time the duration of the period during which the substantially constant skin current $I_S$ has been produced. When the output of that timer reaches the ratio of total dosage $D_T$ of medicament divided by the substantially constant skin current $I_S$, microprocessor 122 is programmed to function as a circuit breaker and disable power source 62, thereby terminating skin current $I_S$ and the migration of additional medicament through skin 112.

For a skin resistance $R_S=10$ kilo-ohms, the following electrical circuit component values and identities in voltage regulator 120 and in indicator circuit 130 produced a substantially invariant voltage V=2.75 volts and a corresponding substantially constant skin current $I_S=0.275$ milliamperes during the course of a therapy period $T_M=280$ minutes:

M=8-pin, 8-bit flash microcontroller PIC 12 F 510-I/SN of the type manufactured by Microchip Technology Inc. of Chandler, Ariz. U.S.A;

D=green light-emitting diode PG 1112 H-TR of the type manufactured by Stanley Electric U.S. Co., Inc. of London, Ohio, U.S.A.;

B=3.0 volt lithium-manganese button cell CR 1025 of the type manufactured by Blueline Electronics Technology Co., Inc. of Hong Kong, R.O.C.;

$R_1$=100 kilo-ohm resistor ERJ-6 GEYJ 104 V of the type manufactured by Panasonic Corporation of North America of Secaucus, N.J. U.S.A.;

$R_2$=300 ohm printed resistor; and

S=pull tab switch fabricated from same polyester film as circuit board 68.

Performance curves for such a voltage regulator 120 and such an indicator circuit 130 are included by way of example among the drawings.

Figures 7A, 7B:
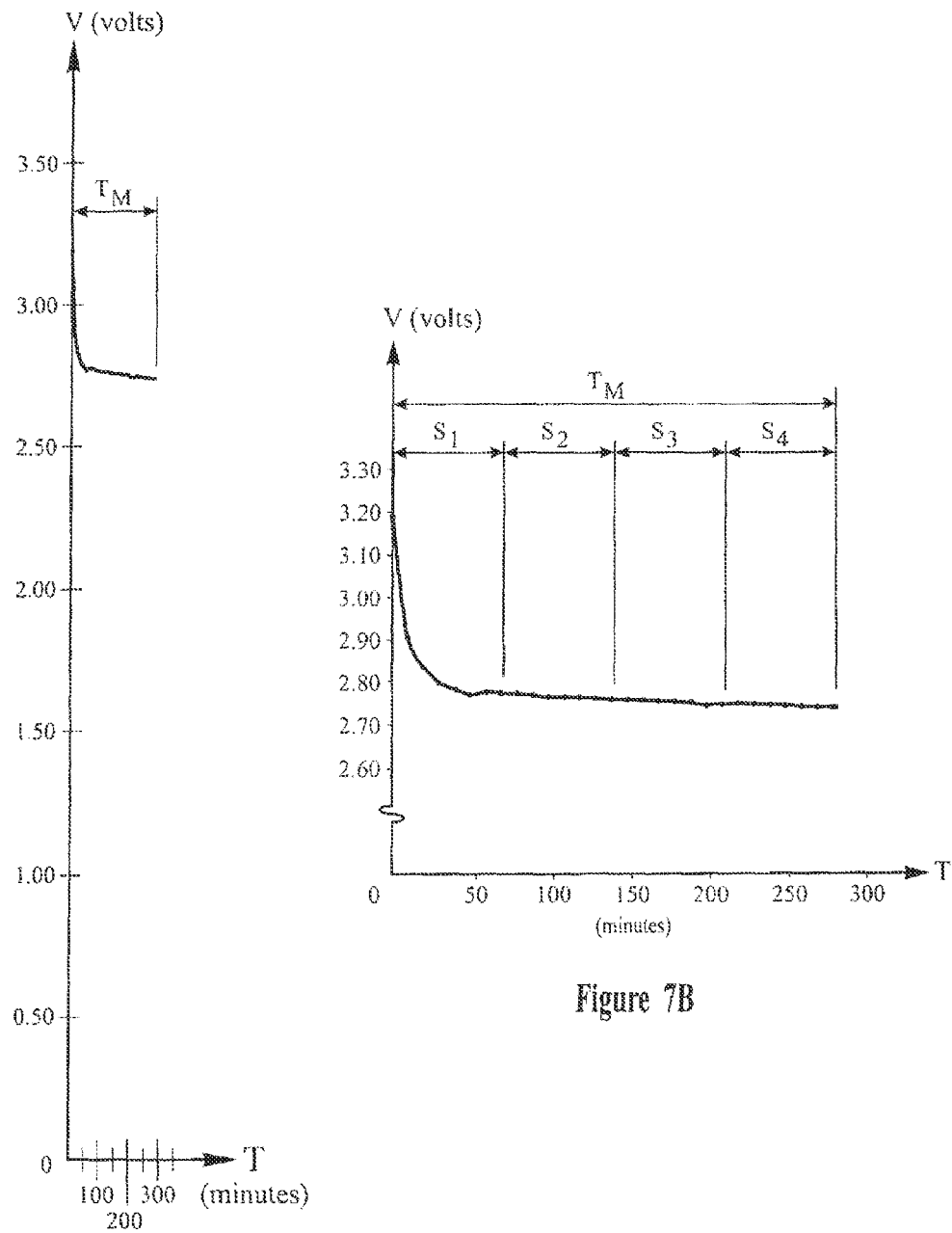
FIGS. 7A and 7B are the same performance curve, but drawn in contrasting respective scales, of a first performance parameter of the electronics of FIG. 6 taken over a predetermined therapy period.

FIGS. 7A and 7B are the same performance curve, but drawn in contrasting respective scales to depict the voltage V applied by voltage regulator 120 across a skin resistance $R_S=10$ kilo-ohms over a predetermined therapy period $T_M$=280 minutes. In FIG. 7B, the enlarged-scale version of the voltage performance curve, therapy period $T_M$ is for convenience of analysis divided into a plurality of four (4) equal therapy subsessions $S_1$, $S_2$, $S_3$, and $S_4$ of 70 minutes each.

At time T=0 minutes, power source 62 is activated by a user through the operation of switch 64. Immediately, but only momentarily, voltage V=3.18 volts, greater even than the nominal 3.00 volt rating of power source 62 when configured as a battery B of the type specified in the above list of electrical circuit component in FIG. 6. From time T=0 minutes, voltage V declines steeply in a seemingly linear manner. By time T=5 minutes, voltage V=3.00 volts. Then, voltage V commences a relatively sharp decline in slope, decaying asymptotically toward the horizontal. At about time T=20 minutes, voltage V arrives at a substantially invariant voltage V=2.75±0.02 volts, which is then sustained by voltage regulator 120 throughout the balance of therapy subsession $S_1$ and all of therapy subsessions $S_2$, $S_3$, and $S_4$ remaining in therapy period $T_M$.

The initial behavior of voltage V depicted in FIGS. 7A and 7B at the commencement of therapy period $T_M$ results from mildly transient start-up performances on the part of power source 62 and the electrical components of voltage regulator 120 and indicator circuit 130. Nonetheless, as will be observed subsequently, in the context of the totality of therapy period $T_M$, that initial transient behavior of voltage V has a negligible effect on the total dosage $D_T$ of medicament administered.

Figures 8A, 8B:
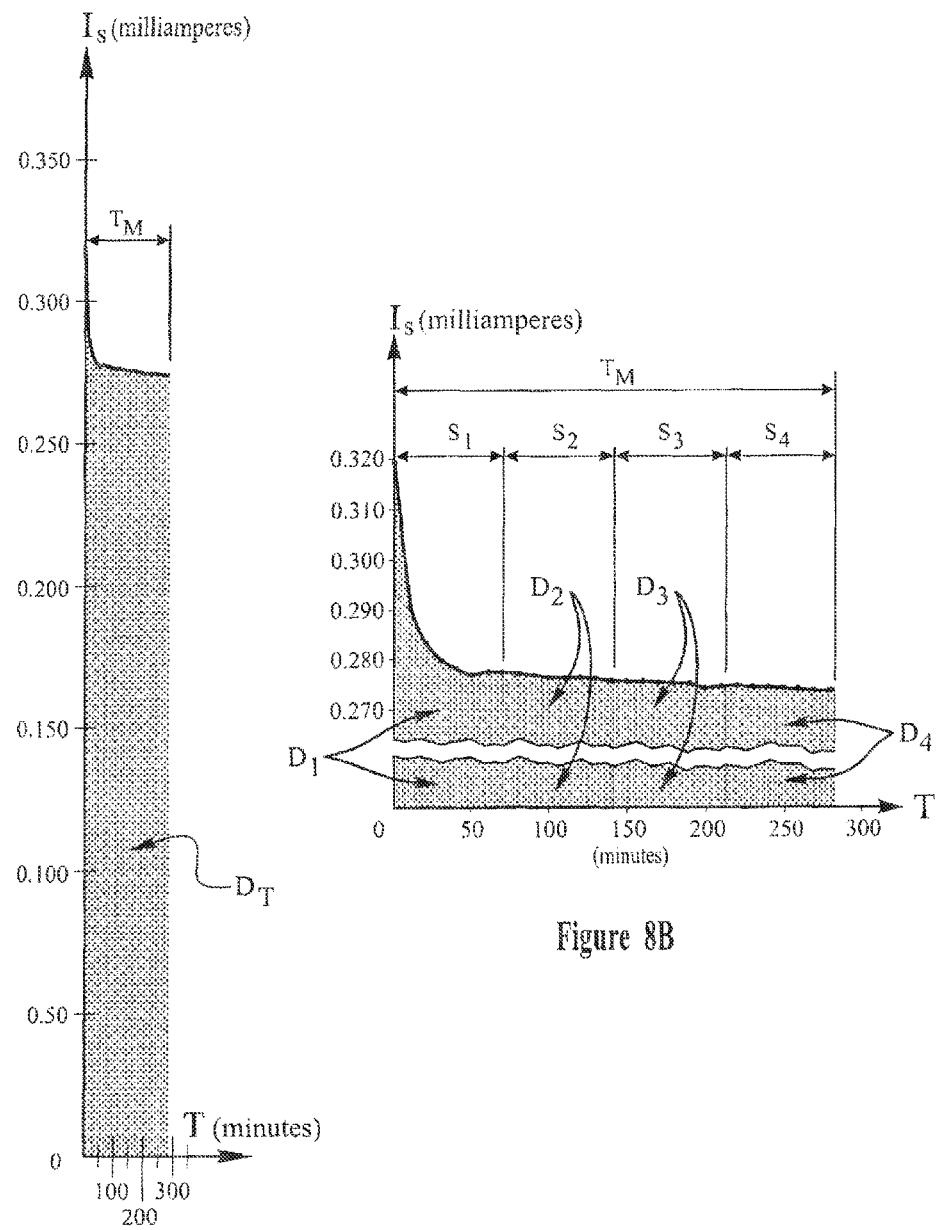
FIGS. 8A and 8B are the same performance curve, but drawn in contrasting respective scales, of a second performance parameter of the electronics of FIG. 6 taken over the same predetermined therapy period used in FIGS. 7A and 7B.

FIGS. 8A and 8B are the same performance curve, but drawn in contrasting respective scales to depict the skin current $I_S$ produced by voltage V depicted in FIGS. 7A and 7B. In FIG. 8B, the enlarged-scale version of the skin current performance curve, therapy period $T_M$ has for consistency of analysis been divided into the same plurality of therapy subsessions $S_1$, $S_2$, $S_3$, and $S_4$ as appeared in FIG. 7B.

The initial transient behavior of voltage V is closely reflected in skin current $I_S$.

At time T=0 minutes, skin current $I_S$=0.318 milliamperes. From time T=0 minutes, skin current $I_S$ declines steeply in a seemingly linear manner. By time T=5 minutes, skin current $I_S$=0.300 milliamperes. Then, skin current $I_S$ commences a relatively sharp decline in slope, decaying asymptotically toward the horizontal. At about time T=20 minutes, skin current $I_S$ arrives at a substantially constant skin current $I_S$=0.275±0.02 milliamperes, which is then sustained throughout the balance of therapy subsession $S_1$ and all of therapy subsessions $S_2$, $S_3$, and $S_4$ remaining in therapy period $T_M$. In the context of the totality of therapy period $T_M$, that initial transient behavior of skin current $I_S$ has a negligible effect on the total dosage $D_T$ of medicament administered.

The area below the performance curve of skin current $I_S$ in FIGS. 8A and 8B from time T=0 minutes until any given time T during therapy period $T_M$ is equal to the cumulative dosage D of medicament administered through that time T. Thus, in FIG. 8A the area beneath the performance curve of skin current $I_S$ between time T=0 minutes and time T=280 minutes at the conclusion of therapy period $T_M$ is identified as the total dosage $D_T$ of medicament administered. To facilitate continued analysis, in FIG. 8B the total dosage $D_T$ of medicament administered has been divided into a plurality of four (4) medicament subdoses $D_1$, $D_2$, $D_3$, and $D_4$, which correspond in a one-to-one manner to the amount of medicament administered during each of therapy subsessions $S_1$, $S_2$, $S_3$, and $S_4$, respectively. Thus, therapy subdose $D_1$ represents the amount of medicament administered in therapy subsession $S_1$; therapy subdose $D_2$ represents the amount of medicament administered in therapy subsession $S_2$; and so forth.

Figure 9:
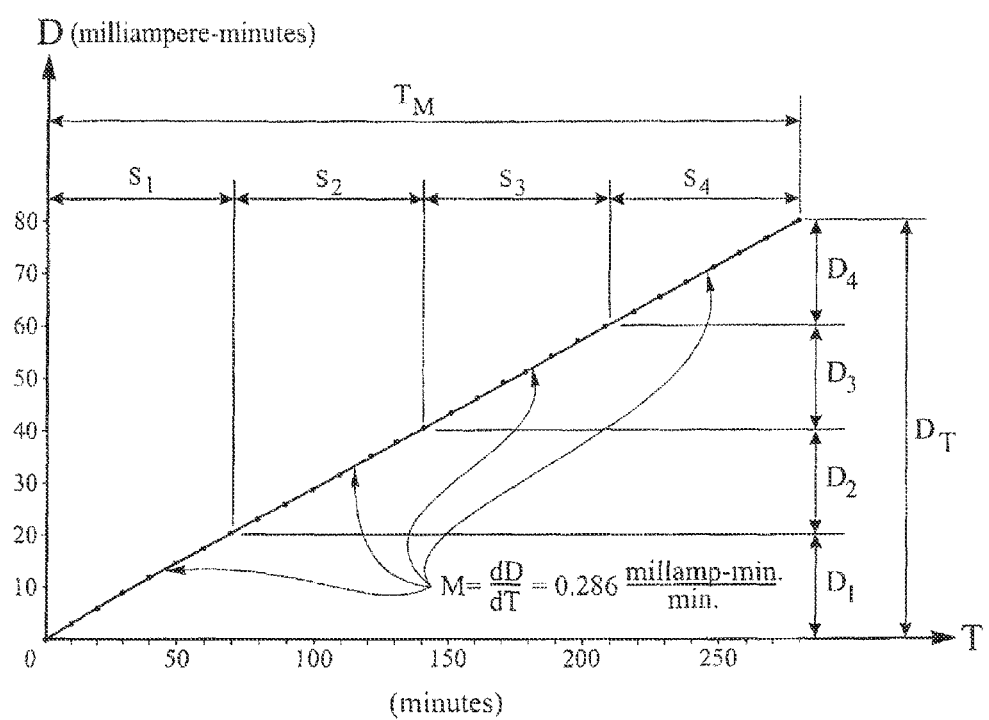
FIG. 9 is a performance curve of a third performance parameter of the electronics of FIG. 6 taken over the same predetermined therapy period used in FIGS. 7A-7B and 8A-8B.

FIG. 9 is a performance curve showing the cumulative dosage D of medicament administered as a result of the imposition of the voltage V of FIGS. 7A-7B across a skin resistance $R_S$=10 kilo-ohms from time T=0 minutes at the start of therapy period $T_M$ until the end of therapy period $T_M$ at time T=280 minutes. The performance curve of FIG. 9 is thus derived directly from FIGS. 8A-8B, being a plot of the value of the area beneath the performance curve of skin current $I_S$ in those drawings. As can be observed, cumulative dosage D is substantially strictly linear, reflecting the administration in each of therapy subsessions $S_1$, $S_2$, $S_3$, and $S_4$ of corresponding equal medicament subdoses $D_1$, $D_2$, $D_3$, and $D_4$ of about 40 milliampere-minutes. Thus, during the entirety of therapy period $T_M$, the circuitry of FIG. 6 administers a total dosage $D_T$=280 milliampere-minutes of medicament at a substantially constant rate of about 0.286 milliampere-minutes per minute, the slope M of the performance curve of cumulative dosage D presented in FIG. 9.

During the administration of a medication using an active medicament patch, such as medicament patch 16, it may become necessary or it may occur accidentally that therapy is interrupted before the end of a full predetermined therapy period $T_M$ during which a corresponding predetermined total dosage $D_T$ of medicament was intended to be administered. This might occur, for example, due to the removal of medicament patch 16 from the skin of the patient. Once the interruption of therapy is detected, and the cause of the interruption remedied, therapy can and should be resumed toward the completion of the administration of total dosage $D_T$ of medicament. Under such circumstances, uncertainty will exist relative to how much medicament was actually administered before the interruption. Correspondingly uncertain will be the amount of additional medicament that needs to be administered once therapy is resumed in order to cumulatively administer total dosage $D_T$ of medicament.

Accordingly, in one aspect of the present invention, an active medicament patch, such as medicament patch 16, is provided with dosage control means carried non-removably on the substrate of the medicament patch for limiting to a predetermined medicament quantity the total medicament migrated iontophoretically from the medicament matrix into the skin of the patient during, what under the circumstances becomes, a plurality of temporally non-contiguous therapy subsessions. The portion of therapy period $T_M$ preceding any interruption thereof and the balance of therapy period $T_M$ that must of necessity be undertaken following such an interruption are examples of a pair of such temporally non-contiguous therapy subsessions.

Yet, it is contemplated that a dosage control means incorporating teachings of the present invention be able to accommodate for any number of interruptions in therapy during any single intended therapy period $T_M$. Such a situation might arise, for example, were it desirable under circumstances like those depicted in the performance curves of FIGS. 7A-9 to interrupt therapy for a brief respite at the end of several or each of therapy subsessions $S_1$, $S_2$, and $S_3$. Such an interruption or interruptions might be needed in order to inspect the skin of the patient at the site of therapy or to adjust the positioning of medicament patch 16 on the skin of the patient.

Accordingly, as shown by way of example in FIG. 6, a dosage control means incorporating teachings of the present invention includes a medicament migration detector that includes microprocessor 122 and sensing resistor 124 electrically coupled as shown to power source 62, return electrode 42, and medicament matrix 30. Such a dosage control means need not necessarily be contained within or associated with circuitry that, like voltage regulator 120, is capable of imposing a substantially invariant voltage V between return electrode 42 and medicament matrix 30. The medicament migration detector continuously monitors the flow of skin current $I_S$ and, thereby, the iontophoretic migration of medicament from medicament matrix 30 into the skin of the patient. As an output, the medicament migration detector produces a continuous measure of the instantaneous rate of that iontophoretic medicament migration.

In combination with such a medicament migration detector, a dosage control means incorporating teachings of the present invention includes a dosage integrator that operates on the output of the medicament migration detector to produce as an output a running cumulative total of the amount of medicament delivered by iontophoretic migration. Such a dosage control means may, for example, be effected in the software in microprocessor 122, or in the alternative may be embodied in software or hardware located elsewhere than within microprocessor 122. A circuit breaker disables power source 62, when the output of the dosage integrator equals the predetermined total dosage $D_T$ associated with the full predetermined therapy period $T_M$. Such a circuit breaker may, for example, be effected in the software in microprocessor 122, or in the alternative may be embodied in software or hardware located elsewhere than within microprocessor 122. In this manner, following any interruption in the administration of medication, the dosage control means resumes monitoring the amount of medication administered where that administration was at the time of the interruption.

Power source 62 may be so electrically coupled between return electrode 42 and medicament matrix 30 as to cause iontophoretic medicament migration from medicament matrix 30 into the skin of the patient to occur at a substantially constant rate. Such would be the case where the capability of a voltage regulator, such as voltage regulator 120, is included among associated electrical circuit components. Under such circumstances, a dosage control means incorporating teachings of the present invention includes, a medicament migration detector as described above and a timer active only when the output of the medicament migration detector exceeds a predetermined minimum rate of medicament migration associated with a closed circuit. Such a timer may, for example, be effected in the software in microprocessor 122, or in the alternative may be embodied in software or hardware located elsewhere than within microprocessor 122. A circuit breaker disables power source 62, when the duration of the activity of the timer equals the ratio of the predetermined total dose $D_T$ of medicament divided by the substantially constant rate of iontophoretic medicament migration being produced It has been found to be helpful to apprise a user of an active medicament patch, such as medicament patch 16, as to the degree to which the administration of any total dosage $D_T$ of medicament has been completed. Accordingly, in another aspect of the present invention, an active medicament patch, such as medicament patch 16, includes therapy status advisement means that is non-removably carried on the substrate of that medicament patch, and that is driven by a power source, such as power source 62. The therapy status advisement means performs the function of communicating to a user the extent of completion of predetermined therapy period $T_M$ during which a medicament is to be iontophoretically delivered from medicament matrix 30 into the skin of a patient.

Accordingly, as shown by way of example in FIG. 6, a therapy status advisement means incorporating teachings of the present invention includes microprocessor 122, light-emitting diode 67, and bias resistor 132 as shown electrically coupled to power source 62, return electrode 42, and medicament matrix 30. In the alternative to a visual indicator, such as light-emitting diode 67, the therapy status advisement means may employ an auditory indicator or a tactile indicator of the type described earlier. The therapy status advisement means need not necessarily be contained within or associated with circuitry that, like voltage regulator 120, is capable of imposing a substantially invariant voltage V between return electrode 42 and medicament matrix 30.

Also included in a therapy status advisement means configured according to teachings of the present invention is a timer that is active only during therapy period $T_M$ and a driver for light-emitting diode 67 that causes light-emitting diode 67 to operate only when the timer is active. Typically, light-emitting diode 67 is operated intermittently to minimize power consumption. Such a timer and such a driver may, for example, be effected in the software in microprocessor 122, or in the alternative may be embodied in software or hardware located elsewhere than within microprocessor 122.

Therapy period $T_M$ may include a sequence of non-overlapping predetermined therapy subsessions, such as therapy subsessions $S_1$, $S_2$, $S_3$, and $S_4$ of therapy period $T_M$ depicted in the performance curves of FIGS. 7B, 8B, and 9. Therapy period $T_M$ may include more or fewer therapy subsessions, and those therapy subsessions need not be of substantially equal duration, as in the case of therapy subsessions $S_1$, $S_2$, $S_3$, and $S_4$. Advantageously, the driver of the therapy status advisement means may then activate light-emitting diode 67, or any auditory or tactile indicator used in place thereof, in a distinct mode of operation during each of the therapy subsessions, respectively. Alternative or in addition thereto, the driver of the therapy status advisement means may cause light-emitting diode 67 or any auditory or tactile indicator used in place thereof, to operate in a contrasting transition mode at the end of a selected one or a selected plurality of the therapy subsessions, including at the end of final therapy subsession $S_4$ at the termination of therapy period $T_M$. Finally, the driver of the therapy status advisement means may cause light-emitting diode 67 or any auditory or tactile indicator used in place thereof, to operate in a contrasting alarm mode when the timer of the therapy status advisement means is deactivated prior to the termination of therapy period $T_M$. Such would be the case where therapy during a full predetermined therapy period $T_M$ is interrupted due to the temporary removal of medicament patch 16 from the skin of the patient.

The overall operation of therapy status advisement means is thus governed by the driver of therapy status advisement means, which activates light-emitting diode 67, or any auditory or tactile indicator used in place thereof, in a discrete variety of operative modes P, each of which is reflective of a foreseeable medicament administration status condition X. Each status condition X thus includes temporal and electrical information, information relative to the time T within therapy period $T_M$ and information relative to the existence or nonexistence of skin current $I_S$ in the skin of the patient. Temporally, status condition X can denote that therapy is in a specific one of a plurality of therapy subsessions, such as therapy subsessions $S_1$, $S_2$, $S_3$, and $S_4$, or that therapy is at the end of a chosen one or of all of those therapy subsessions. Electrically, status condition X denotes whether skin current $I_S$ is flowing, or whether skin current $I_S$ is zero by being less than some predetermined minimum amount chosen to evidence an open circuit. The later would be the case, for example, were the resistance between medicament matrix 30 and return electrode 42 to be detectable as exceeding an arbitrary upper threshold, such as 500 kilo-ohms, which is beyond the range of the likely skin resistance $R_S$ in any patient.

In this light, the operative mode P of light-emitting diode 67, or any auditory or tactile indicator used in place thereof, is a function of status condition X. Presented below is a table listing typical status conditions X and an exemplary operative mode P(X) corresponding to each for a therapy period $T_M$ that is comprised of a non-overlapping sequence of therapy subsessions $S_1$, $S_2$, $S_3$, and $S_4$. An operative alarm mode is produced in light-emitting diode 67 whenever skin current $I_S=0$. Distinct first and second operative transition modes are produced in light-emitting diode 67 half way through therapy period $T_M$ at the end of therapy subsession $S_2$, and at the completion of therapy period $T_M$ when therapy subsession $S_4$ ends.

| Status condition X | Operative mode P(X) |
| --- | --- |
| $S_1$ | One (1) LED-flash of duration $A_1$ at regular intervals of duration $E_1$ |
| $S_2$ | Two (2) LED-flashes of duration $A_1$ at regular intervals of duration $E_1$ |
| $S_3$ | Three (3) LED-flashes of duration A1 at regular intervals of duration $E_1$ |
| $S_4$ | Four (4) LED-flashes of duration $A_1$ at regular intervals of duration $E_1$ |
| $I_S = 0$ (alarm mode) | Continuous patterned LED-flashes at regular intervals of duration $E_2 \gg E_1$, each pattern including an LED-flash of duration $A_1$, an interval of duration $E_1$, and an LED-flash of duration $A_2$ |
| $S_2$ has ended (first transition mode) | Continuous LED-flashes of duration $A_1$ at regular intervals of duration $E_3$ for an extended period of duration $K_1$ |
| $T = T_M$ and $S_2$ has ended (second transition mode) | Continuous LED-flashes of duration $A_1$ at regular intervals of duration $E_3$ for an extended period of duration $K_2$ |

Typical possible durations for the events appearing among the operative modes P(X) in the table above are as follows:
$A_1=0.25$ seconds;
$A_2=1.00$ seconds;
$E_1=0.50$ seconds;
$E_2=10.0$ seconds;
$E_3=5.0$ seconds;
$K_1=120$ seconds; and
$K_2=240$ seconds.

Figure 10:
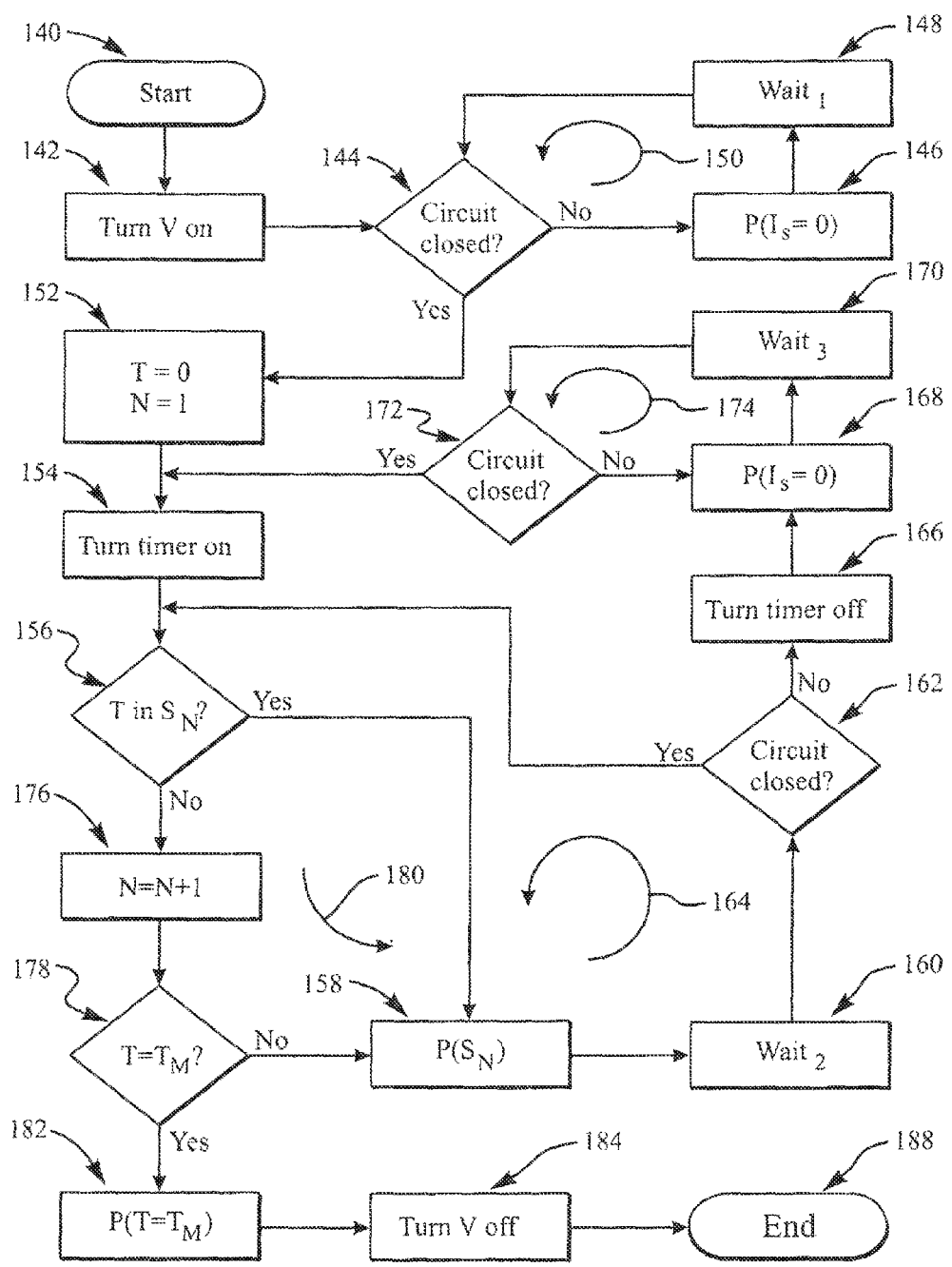
FIG. 10 is a flowchart illustrating selected steps performed by the electronics of FIG. 6.

FIG. 10 is a flowchart of method steps involved in implementing operative mode P(X) as listed in the table above for all status conditions X, other than X="$S_2$ has ended." The activities required to implement operative mode P($S_2$ has ended) have been omitted in FIG. 10 only to avoid redundancy. All of the method steps illustrated may be conducted, by way of example, by software in microprocessor 122 in FIG. 6, or in the alternative by software or hardware located elsewhere.

The depicted methodology commences at initiation oval 140 by turning voltage V on as required in procedure rectangle 142. This occurs when power source 62 is activated by a user through the operation of switch 64. Thereupon, if medicament patch 16 is in place on skin 112 of a patient, voltage regulator 120 should begin to apply voltage V across skin 112 between medicament matrix 30 and return electrode 42, and skin current $I_S$ should begin to flow.

These actions may not always succeed in creating a closed circuit in which a flow of skin current $I_S$ possible. Accordingly, as required by decision diamond 144, microprocessor 122 inquires toward that end. If as a result, microprocessor 122 determines that no skin current $I_S$ is flowing, then as stipulated in procedure rectangle 146, in order to alert a user that medicament patch 16 is not yet operating as intended, the driver of light-emitting diode 67 in microprocessor 122 operates light-emitting diode 67 in operative mode P($I_S=0$), the alarm mode. As specified in procedure rectangle 148, microprocessor 122 then idles for a predetermined period $Wait_1$ during which to permit a user to detect and remedy the situation. After idling for predetermined period $Wait_1$, microprocessor 122 undertakes the inquiry in decision diamond 144 to determine whether skin current $I_S$ has commenced. If not, microprocessor 122 continues repeatedly to operate in a functional loop 150 that includes decision diamond 144, procedure rectangle 146, and procedure rectangle 148.

On any circuit of functional loop 150, if microprocessor 122 detects that skin current $I_S$ has commenced through skin 112, the depicted methodology moves ahead to procedure rectangle 152. Consequently, a timer in microprocessor 122 of the duration of therapy is prepared for activity by setting time T=0, and a counter N identifying the therapy subsession $S_N$ in which therapy is occurring is set to N=1. This signifies that therapy subsession $S_1$ will be the initial therapy subsession. As directed in procedure rectangle 154, the timer in microprocessor 122 is turned on, and time T advances continuously from time T=0 until the timer is turned off.

In decision diamond 156, microprocessor 122 compares the ongoing time T to a schedule of times for the intended therapy subsessions to verify that therapy is occurring in therapy subsession $S_N$ with N=1. If as a result, it is determined that that therapy is occurring in therapy subsession $S_1$, then as specified in procedure rectangle 158, the driver of light-emitting diode 67 in microprocessor 122 operates light-emitting diode 67 in operative mode P($S_1$) to advise the user that medicament patch 16 is operational and that therapy is progressing in therapy subsession $S_1$. According to the above table of operative mode P(X), during therapy subsession $S_1$ light-emitting diode 67 is made to flash once for 0.25 seconds at regular intervals of 0.50 seconds.

In procedure rectangle 160, microprocessor 122 idles for a predetermined period $Wait_e$ and then undertakes the inquiry in decision diamond 162 to determine whether a closed circuit continues to exist in which a flow of skin current $I_S$ is occurring. If it is determined that skin current $I_S$ continues to be flowing, activity returns to decision diamond 156 and continues repeatedly through a functional loop 164 that includes decision diamond 156, procedure rectangle 158, procedure rectangle 160, and decision diamond 162.

On any transit of functional loop 164, if it is determined in decision diamond 162 that no skin current $I_S$ is flowing, the timer in microprocessor 122 is turned off as required in procedure rectangle 166. Time T ceases to advance, until the timer is next turned on. As stipulated in procedure rectangle 168, in order to alert the user that medicament patch 16 is no longer operating as intended, the driver of light-emitting diode 67 in microprocessor 122 operates light-emitting diode 67 in operative mode P($I_S=0$), the alarm mode. Then, as required in procedure rectangle 170, microprocessor 122 idles for a predetermined period $Wait_3$ to allow a user to detect and remedy the situation. After idling for predetermined period $Wait_3$, microprocessor 122 undertakes the inquiry in decision diamond 172 to determine whether skin current $I_S$ has resumed. If not, microprocessor 122 continues repeatedly to operate in a functional loop 174 that includes decision diamond 172, procedure rectangle 168, and procedure rectangle 170.

On any transit of functional loop 174, if microprocessor 122 detects at decision diamond 172 that skin current $I_S$ has recommenced through skin 112, the depicted methodology leaves functional loop 174 and moves ahead to procedure rectangle 154. The timer in microprocessor 122 is again turned on. As a consequence thereof, time T advances continuously once again, but from the time T at which the timer was turned off in procedure rectangle 166. Activity returns to functional loop 164, until such time as in undertaking the inquiry in decision diamond 156, microprocessor 122 compares time T to the schedule of times for the intended therapy subsessions and discovers that therapy is no longer in therapy subsession $S_N$ with N=1.

Thereupon, the illustrated methodology advances to procedure rectangle 176, and microprocessor 122 increases counter N by one; so that N=2. As a consequence, therapy is understood to be starting the next successive therapy subsession $S_{N+1}$, or in other words to be starting therapy subsession $S_2$, which follows therapy subsession $S_1$. In decision diamond 178, microprocessor 122 ascertains whether therapy period $T_M$ has yet fully transpired. If not, the administration of total dosage $D_T$ of medicament has not yet been completed, and the illustrated methodology returns to functional loop 164 by way of procedure rectangle 158, but with N=2. Procedure rectangle 176 and decision diamond 178 thus make up a functional branch 180 by which microprocessor 122 resisters that therapy has advanced into a successive therapy subsession.

On each successive circuit of functional loop 164, the driver of light-emitting diode 67 in microprocessor 122 operates light-emitting diode 67 in operative mode $P(S_2)$ to advise the user that medicament patch 16 is operational and that therapy is progressing in therapy subsession $S_2$. According to the above table of operative mode P(X), during therapy subsession $S_2$ light-emitting diode 67 is made to flash twice for 0.25 seconds at regular intervals of 0.50 seconds. The illustrated methodology continues in functional loop 164, until the inquiry undertaken by microprocessor 122 in decision diamond 156 reveals that therapy subsession $S_2$ has been completed.

Then, by way of a functional branch 180 counter N is again increased by one, and activity resumes, reentering functional loop 164 through procedure rectangle 158. On each occasion that the inquiry in decision diamond 156 diverts activity out of functional loop 164 and through functional branch 180, a successive therapy subsession is commenced.

Eventually, in conducting the inquiry in decision diamond 178 it will be revealed to microprocessor 122 that therapy period $T_M$ has fully transpired, or in other words that time $T=T_M$. As specified in procedure rectangle 182, the driver of light-emitting diode 67 in microprocessor 122 then operates light-emitting diode 67 in operative mode $P(T=T_M)$ in order to alert the user that operation of medicament patch 16 is about to cease. Finally, as called for in procedure rectangle 184, the circuit breaker in microprocessor 122 turns voltage V off by disabling power source 62, and the illustrated methodology concludes in termination oval 188.

The invention may be embodied in other specific forms without departing from the spirit or essential characteristics thereof. The described embodiments are to be considered in all respects only as illustrative and not restrictive. The scope of the invention is, therefore, to be defined by the appended claims, rather than by the foregoing description. All variations from the literal recitations of the claims that are, nonetheless, within the range of equivalency correctly attributable to the literal recitations are, however, to be considered to be within the scope of those claims.

What is claimed is:

1. A transdermal medicament patch comprising:
    (a) a flexible, planar biocompatible substrate having on one side thereof a therapeutic face configured for releasable retention against the skin of a patient;
    (b) a planar medicament matrix secured to said therapeutic face of said substrate interior the periphery thereof, said medicament matrix being susceptible to permeation by medicament, and said medicament matrix effecting electrically conductive engagement with the skin of the patient when said substrate is retained thereupon;
    (c) a return electrode on the same side of said substrate as said medicament matrix interior said periphery of said therapeutic face, said return electrode effecting electrically conductive engagement with the skin of the patient when said substrate is retained thereupon;
    (c) a power source carried on said substrate and being so electrically coupled between said medicament matrix and said return electrode as to cause iontophoretic migration of medicament from said medicament matrix into the skin of the patient; and
    (d) dosage control means carried non-removably on said substrate for limiting to a predetermined medicament quantity the total medicament migrated iontophoretically from said medicament matrix into the skin of the patient during a plurality of temporally non-contiguous therapy subsessions.

2. A medicament patch as recited in claim 1, wherein said dosage control means comprises a medicament migration detector, said medicament migration detector monitoring iontophoretic medicament migration from said medicament matrix into the skin of the patient and producing as an output a continuous measure of the actual rate of said iontophoretic medicament migration.

3. A medicament patch as recited in claim 2, wherein said dosage control means further comprises:
    (a) a dosage integrator operating on said output of said medicament migration detector and producing as an output a running cumulative total of the amount of medicament delivered by said iontophoretic migration; and
    (b) a circuit breaker disabling of said power source, when said output of said dosage integrator equals said predetermined medicament quantity.

4. A medicament patch as recited in claim 2, wherein:
    (a) said power source is so electrically coupled between said medicament matrix and said return electrode as to cause iontophoretic medicament migration from said medicament matrix into the skin of the patient to occur at a substantially constant rate; and
    (b) said dosage control means further comprises:
        (i) a timer active only when the output of said medicament migration detector exceeds a predetermined minimum rate of medicament migration; and
        (ii) a circuit breaker disabling of said power source, when the duration of the activity of said timer equals the ratio of said predetermined medicament quantity divided by said substantially constant rate of iontophoretic medicament migration.

5. A medicament patch as recited in claim 2, wherein said medicament migration detector comprises an electrical current monitor coupled to said return electrode matrix and productive of an output only when electrical current through said return electrode exceeds a predetermined minimum electrical skin current.

6. A medicament patch as recited in claim 5, wherein said electrical current monitor comprises a sensing resistor electrically coupled between said return electrode and said power source.

7. A medicament patch as recited in claim 1, wherein said dosage control means comprises an open circuit detector so electrically coupled between said medicament matrix and said power source as to monitor the circuit created between said medicament matrix and said return electrode through the skin of a patient, when said substrate is retained thereupon.

8. A medicament patch as recited in claim 7, wherein said open circuit detector monitors electrical current flow resistance through the skin of the patient between said medicament matrix and said return electrode, said monitor being productive of an output only when electrical current flow resistance between said medicament matrix and said return electrode is less than a predetermined maximum electrical current flow resistance.

9. A medicament patch as recited in claim 1, further comprising a switch carried on substrate, said switch permitting a user to initiate operation of said power source.

10. A medicament patch as recited in claim 1, further comprising dosing verification means carried non-removably on said substrate for confirming to a user that medicament from said medicament matrix is being delivered iontophoretically into the skin of the patient.

11. A medicament patch as recited in claim 10, further comprising a driver for said dosing verification means, said driver operating said dosing verification means in a distinct delivery confirmation mode during each of said therapy subsessions, respectively.

12. A transdermal medicament patch comprising:
(a) a flexible, planar biocompatible substrate having on one side thereof a therapeutic face configured for releasable retention against the skin of a patient;
(b) a medicament matrix secured to said therapeutic face of said substrate interior the periphery thereof, said medicament matrix effecting electrically conductive engagement with the skin of the patient when said substrate is retained thereupon;
(c) a return electrode on the same side of said substrate as said medicament matrix interior said periphery of said therapeutic face, said return electrode effecting electrically conductive engagement with the skin of the patient when said substrate is retained thereupon;
(d) a power source carried on said substrate and electrically coupled between said medicament matrix and said return electrode; and
(d) therapy status advisement means non-removably carried on said substrate and driven by said power source for communicating to a user the extent of completion of a predetermined therapy period wherein medicament is to be iontophoretically delivered from said medicament matrix into the skin of the patient.

13. A medicament patch as recited in claim 12, wherein said therapy status advisement means comprises a visual indicator.

14. A medicament patch as recited in claim 12, wherein said therapy status advisement means comprises:
(a) a light-emitting diode;
(b) a timer active during said therapy period; and
(c) a driver for said light-emitting diode, said driver causing said light-emitting diode to operate when said timer is active.

15. A medicament patch as recited in claim 14, wherein said driver causes said light-emitting diode to operate intermittently.

16. A medicament patch as recited in claim 14, wherein said therapy period comprises a sequence of non-overlapping predetermined therapy subsessions, and said driver causes said light-emitting diode to operate in a distinct delivery confirmation mode during each of said therapy subsessions, respectively.

17. A medicament patch as recited in claim 16, wherein said therapy subsessions comprise time intervals of substantially equal duration within said therapy period.

18. A medicament patch as recited in claim 16, wherein said driver causes said light-emitting diode to operate in a transition mode at the end of selected of said therapy subsessions.

19. A medicament patch as recited in claim 18 wherein said selected of said therapy subsessions comprises the final of said therapy stages.

20. A medicament patch as recited in claim 14, wherein said therapy status advisement means further comprises a medicament migration detector, said medicament migration detector monitoring actual iontophoretic migration of medicament from said medicament matrix into the skin of the patient and deactivating said timer when said iontophoretic migration is absent.

21. A medicament patch as recited in claim 20, wherein said medicament migration detector comprises an electrical current monitor coupled to said medicament matrix and productive of an output only when electrical current through said medicament matrix exceeds a predetermined minimum electrical skin current.

22. A medicament patch as recited in claim 21, wherein said electrical current monitor comprises a sensing resistor electrically coupled between said medicament matrix and said power source.

23. A medicament patch as recited in claim 20, wherein said driver causes said light-emitting diode to operate in an alarm mode when said timer is deactivated prior to the end of said therapy period.

24. A transdermal medicament patch comprising:
(a) a flexible, planar biocompatible substrate having on one side thereof an upper face and on the other side thereof a therapeutic face configured for releasable retention against the skin of a patient;
(b) a circuit board carried on said upper face of said substrate, said circuit board having on one side thereof a support face and on the other side thereof an attachment face, a portion of said attachment face of said circuit board being nonremovably secured to said upper face of said substrate;
(c) a printed circuit on said support face of said circuit board;
(d) a power source carried on said support face of said circuit board;
(e) an electrode carried on said support face of said circuit board, said electrode being electrically coupled to said power source by said printed circuit; and
(f) an electrode hinge traversing said circuit board intermediate said electrode and said power source for permitting bending of said circuit board between:
(i) a planar state of said circuit board; and (ii) a compact state of said circuit board, wherein a portion of said circuit board is folded over such that two portions of said circuit board are in planar contact with each other.

25. A transdermal medicament patch as recited in claim 24, said attachment face of said circuit board is free of electrical circuit elements.

26. A transdermal medicament patch comprising:
(a) a flexible, planar biocompatible substrate having on one side thereof an upper face and on the other side thereof a therapeutic face configured for releasable retention against the skin of a patient, said substrate having formed therethrough a first electrode aperture and a second electrode aperture separated therefrom;
(b) a circuit board carried on said upper face of said substrate, said circuit board having on one side thereof a support face and on the other side thereof an attachment face configured in part for non-removable securement to said upper face of said circuit board, said circuit board being capable of assuming a planar state and a folded state, in said folded state of said circuit board portions of said attachment face in each of a first region and a nonadjacent second region of said circuit board engage corresponding portions of said attachment face in a third region of said circuit board intermediate said first and second regions;
(c) a printed circuit on said support face of said circuit board;
(d) an active electrode carried on said support face in said first region of said circuit board
(e) a return electrode carried on said support face in said second region of said circuit board;
(f) a power source carried on said support face of said circuit board, said power source being electrically coupled to said active electrode and to said return electrode by said printed circuit; and
(g) an adhesive between said upper face of said substrate and a portion of said attachment face in said third region of said circuit board free of said first region of said circuit board and free of said second region of said circuit board in said folded state of said circuit board.

27. A transdermal medicament patch as recited in claim 26, wherein said adhesive secures said circuit board of said upper face of said substrate in said folded state of said circuit board with said active electrode accessible from said therapeutic face of said substrate through said first electrode aperture and with said return electrode accessible from said therapeutic face of said substrate through said second electrode aperture.

28. A transdermal medicament patch as recited in claim 26, wherein an electrical circuit element is carried on said support face of said third region of said circuit board, and said electrical circuit element is electrically coupled to said power source by said printed circuit.

29. A transdermal medicament patch as recited in claim 26, wherein said circuit board is comprised of a flexible polyester film.

30. A transdermal medicament patch as recited in claim 26, said attachment face of said circuit board is free of electrical circuit elements.

* * * * *